(12) United States Patent
Dean

(10) Patent No.: US 10,695,048 B2
(45) Date of Patent: Jun. 30, 2020

(54) SLACK REMOVAL IN SUTURE CONSTRUCTS FOR TISSUE REPAIR

(71) Applicant: Ryan Dean, Niwot, CO (US)

(72) Inventor: Ryan Dean, Niwot, CO (US)

(73) Assignee: Ryan Dean, Niwot, CO (US)

(*) Notice: Subject to any disclaimer, the term of this patent is extended or adjusted under 35 U.S.C. 154(b) by 96 days.

(21) Appl. No.: 16/070,194

(22) PCT Filed: Mar. 2, 2018

(86) PCT No.: PCT/US2018/020592
§ 371 (c)(1),
(2) Date: Jul. 13, 2018

(87) PCT Pub. No.: WO2018/164943
PCT Pub. Date: Sep. 13, 2018

(65) Prior Publication Data
US 2020/0000454 A1    Jan. 2, 2020

Related U.S. Application Data

(60) Provisional application No. 62/467,232, filed on Mar. 5, 2017.

(51) Int. Cl.
*A61B 17/04* (2006.01)
*A61F 2/08* (2006.01)
*A61B 90/00* (2016.01)
*A61B 17/06* (2006.01)

(52) U.S. Cl.
CPC ...... *A61B 17/0401* (2013.01); *A61B 17/0485* (2013.01); *A61F 2/0811* (2013.01); *A61B 2017/0496* (2013.01); *A61B 2017/0618* (2013.01); *A61B 2090/0807* (2016.02)

(58) Field of Classification Search
CPC . A61F 2/0811; A61F 2002/0817–0888; A61B 17/04–0493; A61B 2017/0403–0498
See application file for complete search history.

(56) References Cited

U.S. PATENT DOCUMENTS

| 5,035,701 | A | 7/1991 | Kabbara |
| 5,454,834 | A | 10/1995 | Boebel |
| 5,573,543 | A | 11/1996 | Akopov |
| 8,182,495 | B2 * | 5/2012 | DiStefano .............. A61B 17/04 606/139 |

(Continued)

*Primary Examiner* — Katherine M Shi
(74) *Attorney, Agent, or Firm* — Holzer Patel Drennan

(57) ABSTRACT

Utilities (e.g., systems, methods, etc.) for reducing or limiting slack in stitching or suture constructs secured to tissues in a manner that limits the need for surgeons to physically pull on patients' muscles to remove such slack and that may ultimately reduce recovery time for patients. In one aspect, a method of creating or anchoring a suture construct (e.g., a method of stitching) in tissue in a manner that produces first and second opposite portions of the construct that can be pulled apart in any appropriate manner to apply a tension in the construct to remove slack therein substantially free of pulling on patients' muscles to remove such slack is disclosed. The present utilities also describe a tool that can be used to automatically apply a predetermined level of tension to a suture construct to remove slack therein.

14 Claims, 19 Drawing Sheets

(56) References Cited

U.S. PATENT DOCUMENTS

| | | |
|---|---|---|
| 8,298,247 B2 | 10/2012 | Sterrett |
| 8,540,734 B2 | 9/2013 | Hoof |
| 8,603,113 B2 | 12/2013 | Hamilton |
| 9,955,980 B2 * | 5/2018 | Norton ............... A61B 17/0401 |
| 2012/0046693 A1 * | 2/2012 | Denham ............ A61B 17/0401 |
| | | 606/232 |
| 2012/0265219 A1 | 10/2012 | Rushdy |
| 2014/0343604 A1 | 11/2014 | Frank |
| 2016/0175088 A1 * | 6/2016 | Sengun ..................... A61F 2/08 |
| | | 623/13.17 |
| 2017/0224327 A1 | 8/2017 | Tanner |
| 2017/0296328 A1 | 10/2017 | Albertorio |
| 2019/0038276 A1 * | 2/2019 | Jackson ............. A61B 17/0401 |

\* cited by examiner

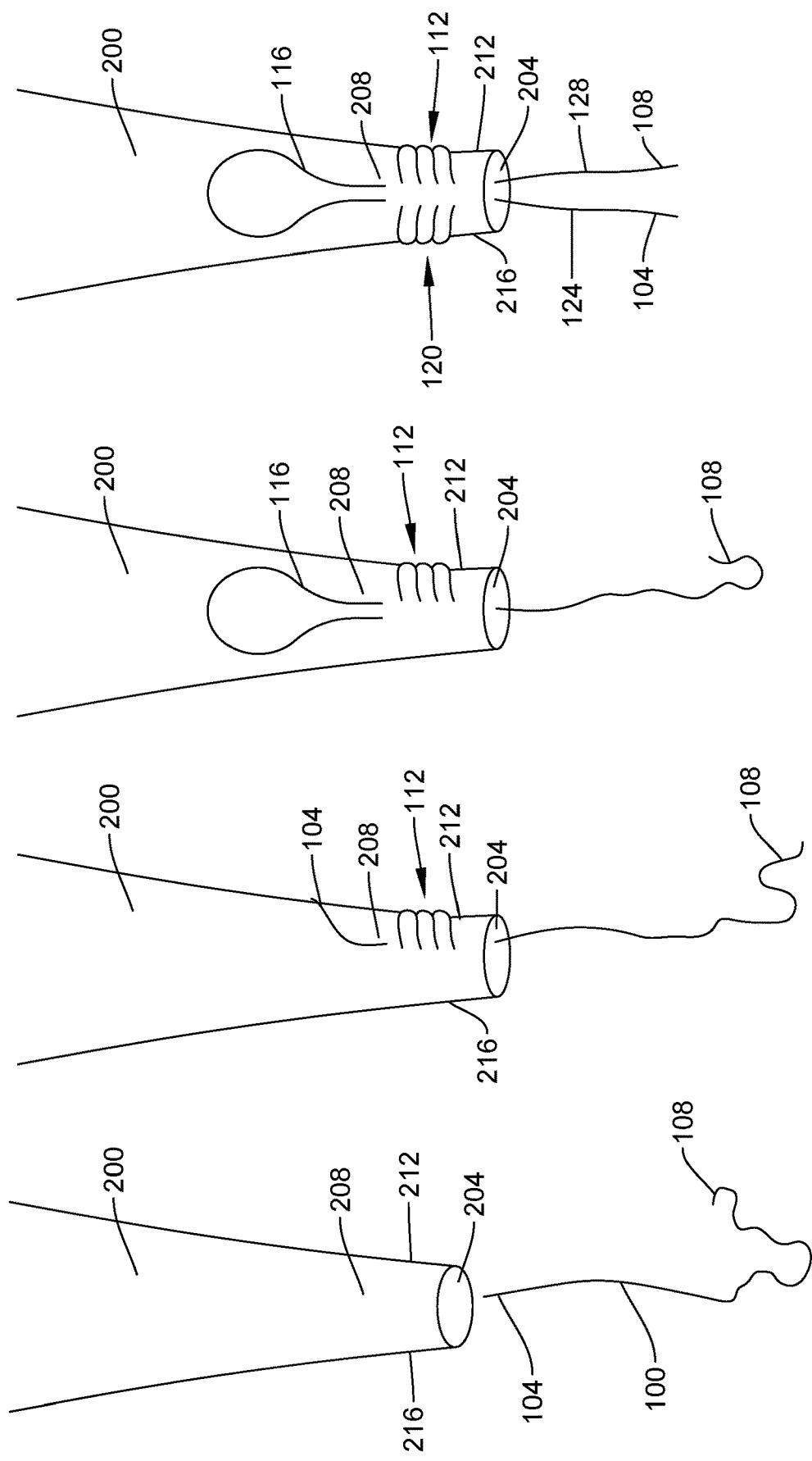

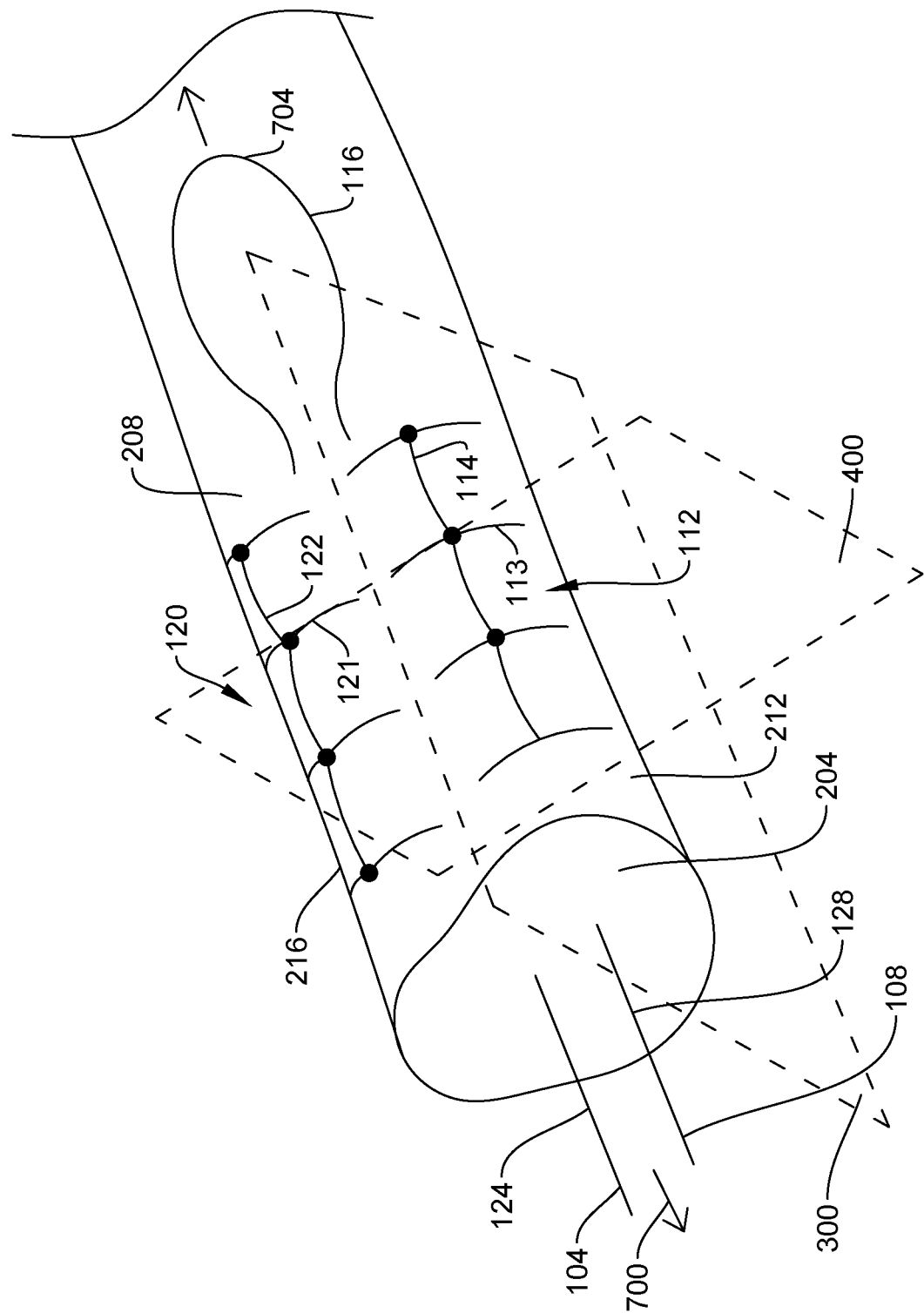

SLACK REMOVAL IN SUTURE CONSTRUCTS FOR TISSUE REPAIR

CROSS REFERENCE TO RELATED APPLICATION

This application is a National Stage Application under 35 U.S.C. 371 of International Application No. PCT/US18/20592, entitled "SLACK REMOVAL IN SUTURE CONSTRUCTS FOR TISSUE REPAIR CROSS," and filed on Mar. 2, 2018, which claims the benefit of U.S. Patent App. No. 62/467,232, entitled "DEVICE AND METHOD FOR REMOVING SLACK IN TENDON REPAIR SUTURE CONSTRUCTS," and filed on Mar. 5, 2017, the entire contents of which is incorporated herein by reference in its entirety.

BACKGROUND

1. Field of the Invention

The present invention generally relates to the repair of tissue such as tendons and ligaments and, more particularly, to suture constructs that facilitate such repair.

2. Relevant Background

The human body contains a wide variety of soft tissue connections to bone, such as tendons connecting muscles to bones and ligaments connecting bones to other bones. Excessive strain can tear or even completely sever the connection between the soft tissue and bone. In many situations, a surgical procedure may be required to reattach the soft tissue to the bone. For example, tendon rupture is a common problem in orthopedics. Tendons are typically repaired with sutures in a variety of configurations. One concern post repair is the amount of "gap formation" or in other words the amount of separation or slack that occurs between the two tendon ends when they are subjected to tension by the patient post tissue repair. Suture configurations, or patterns, are typically chosen for their properties in resistance to gap formation and in relation to ultimate strength.

SUMMARY

Mechanisms of gap formation can include suture tear out, suture material elasticity, knot failure, suture slack and the like. Even after selecting and implementing the particular suture construct based on its resistance to gap formation and in relation to its ultimate strength, surgeons still attempt to remove remaining slack in the construct. Such remaining slack often results from the compressible nature of tissue. However, surgeons are generally only able to remove slack to the extent that they can physically pull on the suture construct, thus leaving remaining slack in the construct that is often not visible to the naked eye. Also limiting the amount of slack that surgeons can remove from suture constructs is the desire to limit damage to surrounding patient tissue. Furthermore, some stitching methods such as the Krackow stitching method and the like include a plurality of adjacent, interlocking loops that naturally tend to resist slack removal when pulled on at one end by surgeons. After the repair is complete, the remaining slack is then cinched down when the patient loads the newly repaired tendon or other tissue. This cinching down can lead to extrusion of the suture out of tissue, resulting in gap formation between the adjacent tissue portions (or between adjacent tissue and bone) and ultimately having a negative effect on rehabilitation.

In view of at least the foregoing, the inventor has developed a new stitching construct, method, and device that serve to reduce or limit slack in stitching constructs secured to tissues in a manner that limits the need for surgeons to physically pull on patients' muscles to remove such slack and that ultimately reduces recovery time for patients. Broadly, disclosed herein is a suture construct that allows tension to be applied to the construct (for reducing slack therein) between one portion of the construct and another portion of the construct rather than from one portion of the construct and a portion of the patient's anatomy (e.g., muscle, other tissue, etc.) as is done in existing procedures. Stated differently, the suture construct and method of creating the suture construct disclosed herein allow for tensioning of the construct in a manner that is substantially free of putting tension on the muscle or other tissue origin. Furthermore, the disclosed tool allows surgeons to apply a specific, predetermined tension to the suture construct that is higher than that achievable by hand and that can be calibrated to any appropriate optimal tension for gap-formation resistance based on, for instance, biomechanical laboratory studies.

In one aspect, a method of anchoring a suture construct into tissue includes inserting a first free end of a flexible strand into a first portion of a tissue; using the first free end of the flexible strand to create one or more stitches in the tissue; exiting a second portion of the tissue with the first free end of the flexible strand, the one or more stitches being disposed between the first and second portions of the tissue; creating a loop with a portion of the flexible strand that has exited the second portion of the tissue; inserting the first free end of the flexible strand into the second portion of the tissue; maintaining at least a portion of the loop outside of the second portion of the tissue after inserting the first free end of the flexible strand into the second portion of the tissue; exiting the first portion of the tissue with first free end of the flexible strand; and simultaneously applying a) a first force to i) a first portion of the flexible strand disposed between the tissue and the first free end of the flexible strand and ii) a second portion of the flexible strand disposed between the tissue and a second free end of the flexible strand and b) a substantially opposite second force to the loop to tighten the one or more stitches against the tissue and thereby reduce slack in the flexible strand.

In one arrangement, the one or more stitches may be a first series of stitches and the method may further include, after the maintaining and before the exiting the first portion of the tissue with first free end of the flexible strand, using the first free end of the flexible strand to create a second series of stitches in the tissue. For instance, the first series of stitches may be disposed on a first lateral side of the tissue and the second series of stitches is disposed on an opposite second lateral side of the tissue. In one embodiment, the method may further include mounting the loop on a first arm of a tool and mounting the first and second portions of the flexible strand on a second arm of the tool, where the simultaneously applying includes manipulating the tool to force at least the first arm away from the second arm to thereby apply the first and second forces. For instance, the manipulating may include manipulating a first handle member of the tool to force at least the first arm away from the second arm (e.g., squeezing the first handle member towards a second handle member of the tool to force at least the first arm away from the second arm). In one arrangement, the method may further include releasing the first handle member when the first arm contacts an indicator member that is attached to the first handle member, where contact between the first arm and the indicator member indicates that a desired level of tension has been applied to the flexible strand between the loop and the first and second portions of the flexible strand.

In another aspect, a suture construct for use in the repair of a tissue includes a first portion of a flexible strand that is configured to be disposed between a first portion of the tissue and a first free end of the flexible strand; a second portion of the flexible strand that is configured to be disposed between the first portion of the tissue and a second free end of the flexible strand; a series of stitches of the flexible strand that are configured to be cinched over a surface of the tissue; and a loop of the flexible strand that is configured to protrude from a second portion of the tissue that is opposite the first portion of the tissue, wherein the series of stitches is disposed between a) the loop and b) the first and second portions of the flexible strand.

In one arrangement, a combination includes the above suture construct and a tool engaged with the suture construct that is configured to simultaneously apply a) a first force to the first and second portions of the flexible strand and b) a substantially opposite second force to the loop for tightening the one or more stitches against the tissue and thereby reducing slack in the flexible strand. For instance, the tool may include a first arm on which the loop of the flexible strand is secured and a second arm on which the first and second portions of the flexible strand are secured, where manipulation of at least the first arm away from the second arm applies the first and second forces.

In a further aspect, a tool for use in applying a tension to a suture construct includes a first portion including a first handle member and a first arm; where the first arm includes an extension member that is configured to receive a first portion of the suture construct, and an indicator member. The tool also includes a second portion including a second handle member and a second arm that is configured to receive an opposite second portion of the suture construct. The first portion is pivotally attached to the second portion for pivotal movement about a pivot axis such that moving the first handle member towards the second handle member induces a) movement of first arm away from the second arm to increase tension in the suture construct and then b) elastic deformation of the extension member towards the second arm and into contact with a contact portion of the indictor member to indicate that a desired level of tension in the suture construct has been reached.

In addition to the exemplary aspects and embodiments described above, further aspects and embodiments will become apparent by reference to the drawings and by study of the following descriptions.

BRIEF DESCRIPTION OF THE DRAWINGS

FIG. 1a is a schematic view of a first free end of a flexible strand that is about to be inserted into a first portion of a tissue.

FIG. 1b is similar to FIG. 1a, but after the first free end of the flexible strand has been used to create a first series of stitches in the tissue and has then exited an opposite second portion of the tissue.

FIG. 1c is similar to FIG. 1b, but after the first free end has been manipulated to create a loop in the flexible strand.

FIG. 1d is similar to FIG. 1c, but after the first free end of the flexible strand has been used to create a second series of stitches in the tissue and has then exited the first portion of the tissue to create a suture construct.

FIG. 3 is a perspective view of the tissue and suture construct of FIG. 1d.

FIG. 6b is a second perspective view of the tool of FIG. 6a.

FIG. 10b is a second perspective view of the tool of FIG. 10a.

FIG. 13b is a second perspective view of FIG. 13a.

DETAILED DESCRIPTION

Many injuries occur in which a patient's tissue (e.g., tendon, ligament, etc.) separates from another body structure (e.g., bone) or even partially or fully ruptures itself. To repair such injuries, it is often necessary to utilize one or more flexible strands (e.g., sutures) to create an anchor in the tissue (e.g., a suture construct) that can be used to reattach the tissue to the ruptured portion of the tissue and/or to a bone. Existing manners of creating suture constructs typically result in excess levels of slack in the suture construct which can lead to gap formation in the construct upon the patient initially loading the tissue after surgery. Such gap formation can negatively affect rehabilitation and ultimate outcome. Furthermore, attempts by surgeons to reduce slack in existing suture constructs often results in inadequate tensioning.

The present disclosure is generally directed to various utilities (e.g., systems, methods, etc.) for use in reducing or limiting slack in stitching or suture constructs secured to tissues in a manner that limits the need for surgeons to physically pull on patients' muscles to remove such slack and that ultimately reduces recovery time for patients. As discussed herein, the present utilities include a method of creating or anchoring a suture construct (e.g., a method of stitching) in tissue in a manner that produces first and second opposite portions of the construct that can be pulled apart in any appropriate manner to apply a tension in the construct to remove slack therein substantially free of pulling on patients' muscles to remove such slack. The present utilities also describe a tool that can be used to automatically apply a predetermined level of tension to a suture construct to remove slack therein.

Figure 5:
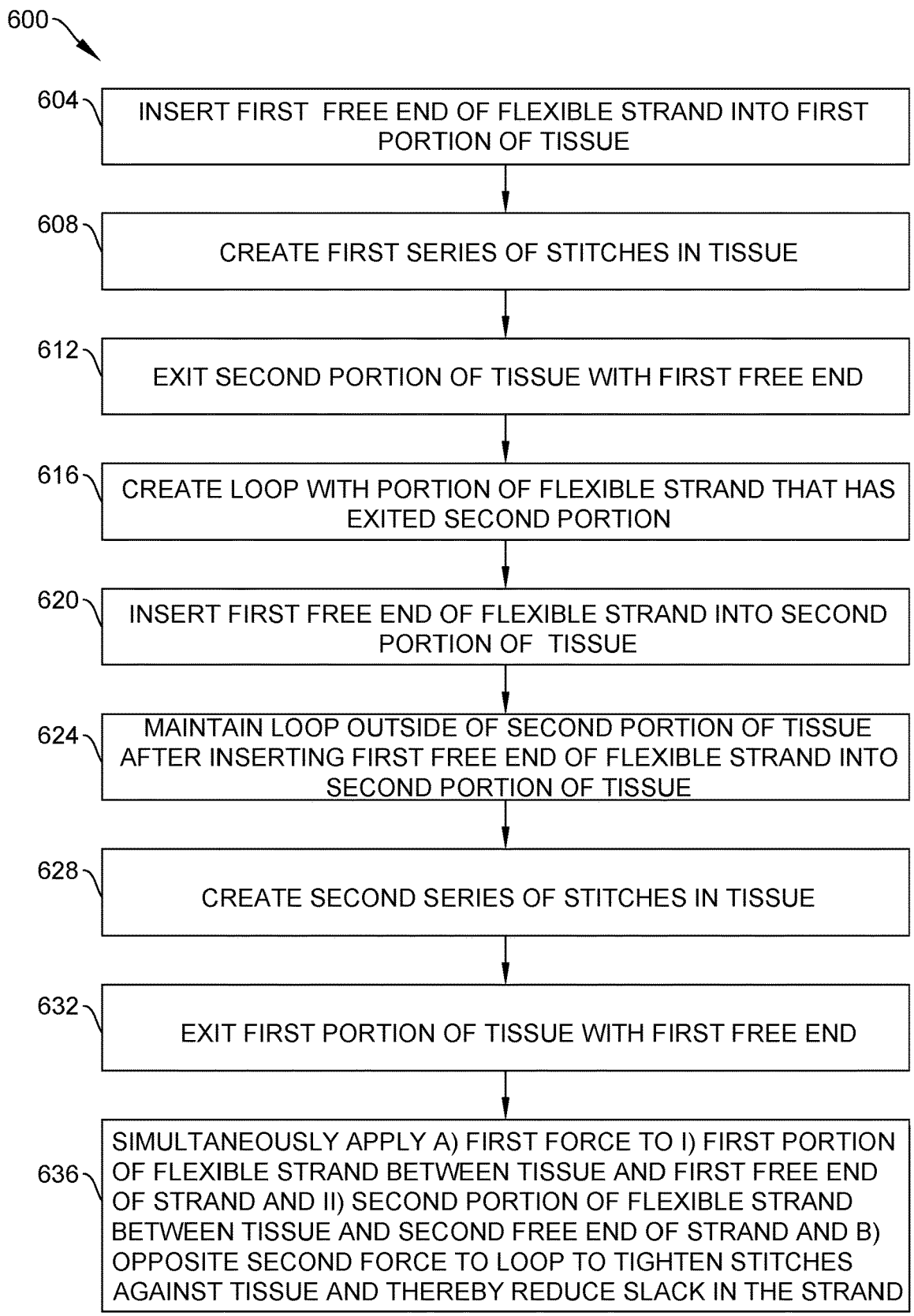
FIG. 5 is flow diagram of a method of anchoring a suture construct into tissue with reduced levels of slack according to one embodiment.

In this regard, FIGS. 1a-1d illustrate a process of creating a suture construct in tissue that creates first and second opposite portions that allow the construct to be pulled in first and second substantially opposite direction to reduce slack in the construct while FIGS. 2a-2d illustrate a process of pulling the construct in the first and second substantially opposite directions to remove the slack and then tying down the construct to maintained the reduced slack levels in the construct. Reference will also be made to FIG. 5 which presents a flow diagram of a method 600 of anchoring a suture construct into tissue in a manner that results in reduced levels of slack therein to inhibit subsequent post-repair gap formation.

At 604, the method 600 may include inserting (e.g., using any appropriate needle, not shown) a first free end 104 of a flexible strand 100 (e.g., FiberWire® suture, LabralTable® suture, FiberTape® suture, etc.) into a first portion 204 of a piece of tissue 200 at or near which a suture construct is to be created in the tissue. See FIG. 1a. The tissue 200 may broadly be any body tissue (e.g., tendon, ligament, labrum) into which it is necessary to anchor a suture construct for use in repairing a bodily injury that involves the tissue (e.g., rupture, tear, etc.). The method 600 may then include creating 608 one or more stitches (e.g., throws) in the tissue such as a first series 112 of stitches. See FIG. 1b. For instance, adjacent stitches in the first series 112 of stitches may be looped together and/or interlocked in any appropriate manner such as using a whipstitch method, the Krackow stitching method, and/or the like. In one arrangement, each stitch loop may be individually tensioned by hand to reduce residual slack.

After the first series 112 of stitches has been created 608 in the tissue, the method 600 may include exiting 612 a second portion 208 of the tissue with the first free end 104 of the flexible strand 100, creating 616 a loop 116 with a portion of the flexible strand 100 that has exited the second portion 208 of tissue, inserting 620 the first free end 104 of the flexible strand 100 into the second portion 208, and maintaining 624 the loop 116 outside of the second portion 208 of tissue. See FIGS. 1b-1c. In one arrangement, the loop 116 may be of any appropriate size such as at least 1 cm in circumference, or more specifically such as at least 3 cm in circumference. In one arrangement, the loop 116 may be no larger than about 20 cm in circumference. The second portion 208 of tissue may broadly be another portion of the tissue 200 that is spaced from the first portion 204. For instance, in the case where the tissue 200 is a segment of a patient's tendon and the first portion 204 is a free end of such segment, the second portion 208 may be a top of such segment that is spaced from the end (as illustrated in the figures) along a longitudinal axis (not shown) of the tissue 200. However, the first and second portions 204, 208 may assume various other portions of the tissue 200 consistent with the teachings presented herein.

The method 600 may then include creating 628 one or more additional stitches in the tissue 200 such as a second series 120 of stitches. See FIGS. 1d and 2a. The second series 120 of stitches may be the same type as or a different type than the first series 112 of stitches. In one arrangement, the first series 112 of stitches may generally be created over and anchored within a first lateral side 212 of the tissue between the first and second portions 204, 208 and the second series 120 of stitches may generally be created over and anchored within an opposite second lateral side 216 of the tissue between the first and second portions 204, 208. For instance, a reference plane 300 passing through the tissue 200 and intersecting the first and second portions 204, 208 may generally separate the first and second lateral sides 212, 216 such that the first and second series 112, 120 of stitches are generally disposed on opposite sides of the reference plane 300. In one arrangement, the first and second series 112, 120 of stitches may include respective lateral portions 113, 121 that generally extend substantially perpendicular to the reference plane 300, and connecting portions 114, 122 that extend substantially parallel to the reference plane 300 and that interconnect adjacent ones of the lateral portions 113, 121. Adjacent lateral portions 113, 121 may be spaced by any appropriate amount such as, merely for purposes of example, 5 mm or the like. In one arrangement, the initial lateral portion 113 of the first series of stitches 112 may be spaced from the end of the tissue 200, such as, merely for purposes of example, 10 mm or the like.

After creation 628 of the second series 120 of stitches and exiting 632 of the first portion 204 of tissue with the first free end 104 of the flexible strand 100, the method 600 may include simultaneously applying 636 a) a first force 700 in a first direction to i) a first portion 124 of the flexible strand 100 disposed between the tissue 200 and the first free end 104 of the flexible strand 100 and ii) a second portion 128 of the flexible strand 100 disposed between the tissue 200 and a second free end 108 of the flexible strand 100 and b) a substantially opposite second force 704 in an opposite second direction to the loop 116 to tighten the one or more stitches against the tissue 100 and thereby reduce slack in the flexible strand 100. Compare FIGS. 2a and 2b and note how the tissue 200 has been compressed in FIG. 2b relative to FIG. 2a due to cinching of the stitches.

In other words, the loop 116 can be used as one anchor for tensioning the suture construct (the first and second series 112, 120 of stitches) while the first and second portions 124, 128 can be used as an opposite anchor for tensioning the suture construct in a manner that is substantially free of applying tension to surrounding muscles attached to the tissue; this is in contrast to existing manners of reducing slack in suture constructs that utilize the patient's muscle or other body structure as one anchor and first and second free ends of a strand as the other anchor which results in direct transfer of possibly dangerous tension levels being applied directly to surrounding tissues and other portions of the patient's anatomy. Furthermore, simultaneously applying the above-discussed first and second forces 700, 704 advantageously substantially overcomes the natural resistance to slack removal present in the Krackow and other locking suture constructs when only pulled on from one end.

Broadly, the first and second forces 700, 704 may be selected to apply a tension load to the suture construct that cinches the stitches about the tissue to reduce slack in the construct but that is less than the ultimate strength of the material(s) making up the flexible strand 100. For instance, the first and second forces 700, 704 may be applied in directions that are generally or substantially parallel to the reference plane 300. In one arrangement, application of the first and second forces 700, 704 as discussed above may induce each of the lateral portions 113, 121 of the stitches to apply cinching forces about respective slices of the tissue 200 that are non-parallel to the reference plane. For example, each tissue slice may reside in a different respective reference plane 400 (only one illustrated in FIG. 3 in the interest of clarity), where each such reference plane 400 may be non-parallel (e.g., substantially perpendicular in one arrangement) to the reference plane 300. Application of the first and second forces 700, 704 may also induce each of the connecting portions 114, 122 of the stitches to apply cinching forces about respective slices of the tissue 200 that are, for instance, parallel to the reference plane 300. In other arrangements, however, the connecting portions 114, 122 may generally be oriented non-parallel to the reference plane 300 such that application of the first and second forces 700, 704 induces such connecting portions 114, 122 to apply cinching forces about tissue slices that are non-parallel to the reference plane 300.

After the first and second forces 700, 704 have been applied as discussed above to reduce slack in the construct, the construct may be considered "pre-tensioned." While frictional forces between the flexible strand 100 and the tissue 200 often substantially maintain such pre-tensioned state of the suture construct, the loop 116 may be severed to create third and fourth free ends 132, 136 and then third and fourth portions 140, 144 of the strand 100 may be cinched down against the tissue 200 and then tied together in one or more knots 148 (e.g., square knots) to further maintain such pre-tensioned state. See FIGS. 2c-2d. The first and second portions 124, 128 of the flexible strand 100 may then be secured to one or more body structures or components (e.g., bone, other portion of ruptured tissue, etc.) in any appropriate manner. In one arrangement, one of the first and second free ends 104, 108 may be inserted into such other body structure/component in the manner discussed above to create a suture construct with reduced slack. Thereafter, the one of the first and second free ends 104, 108 may be secured to the other of the first and second free ends 104, 108 (e.g., via one or more knots) to complete the repair. Other securement methods are also envisioned and encompassed herein.

Figure 2B:
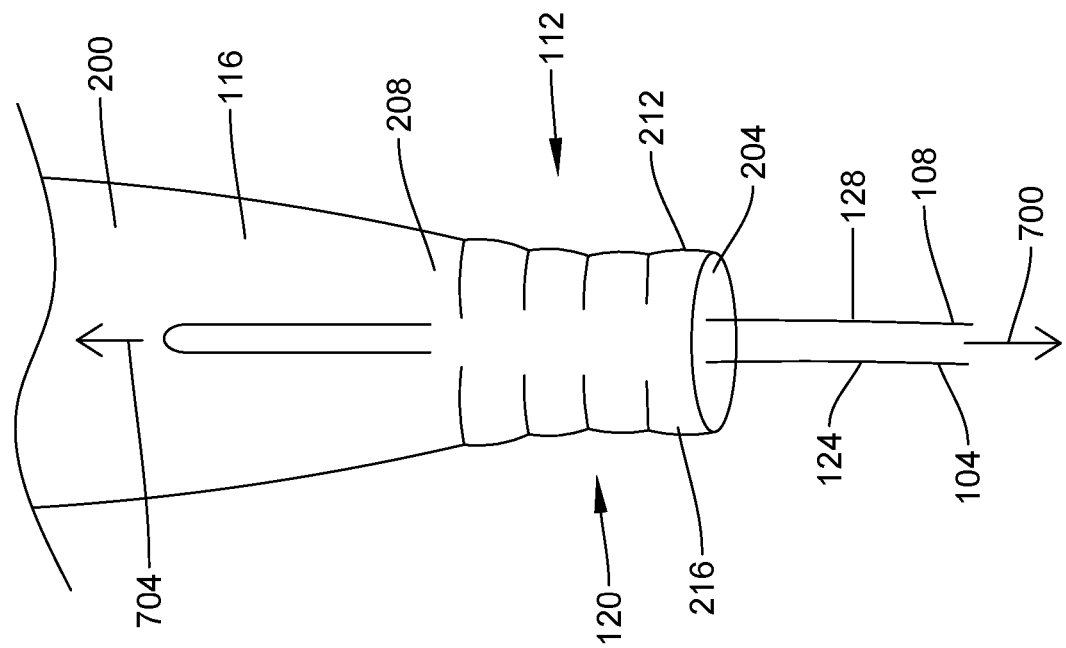
FIG. 2b is similar to FIG. 2a but after a first force has been applied to a first portion of the strand between the first free end and the tissue and second portion of the strand between a second free end and the tissue and a substantially opposite second force has been applied to the loop.
Figure 2A:
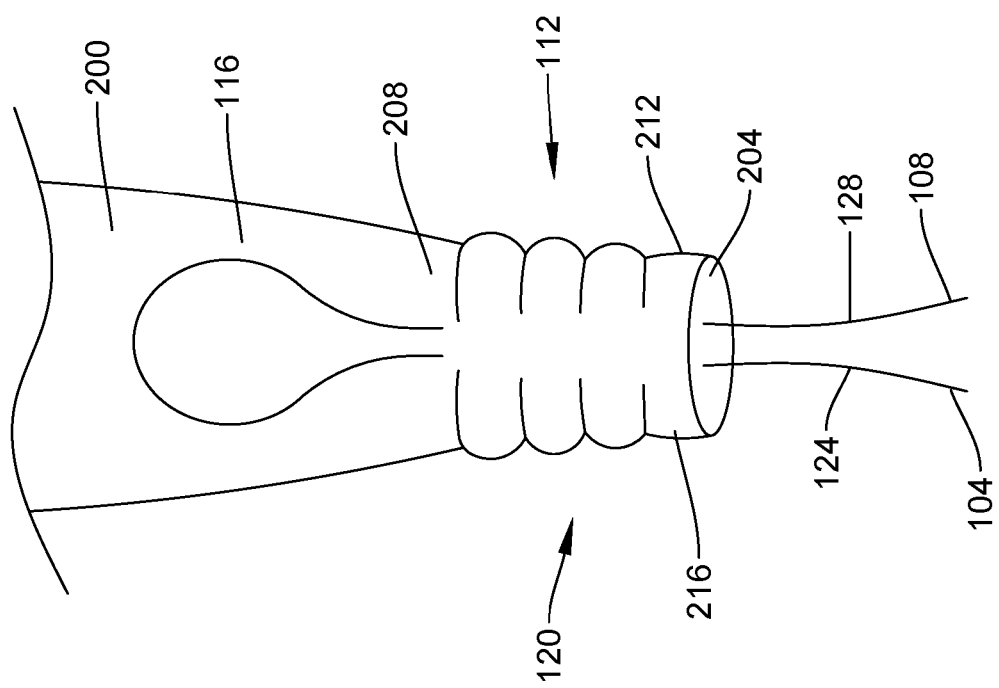
FIG. 2a is a close-up view of the suture construct of FIG. 1d.
Figure 2D:
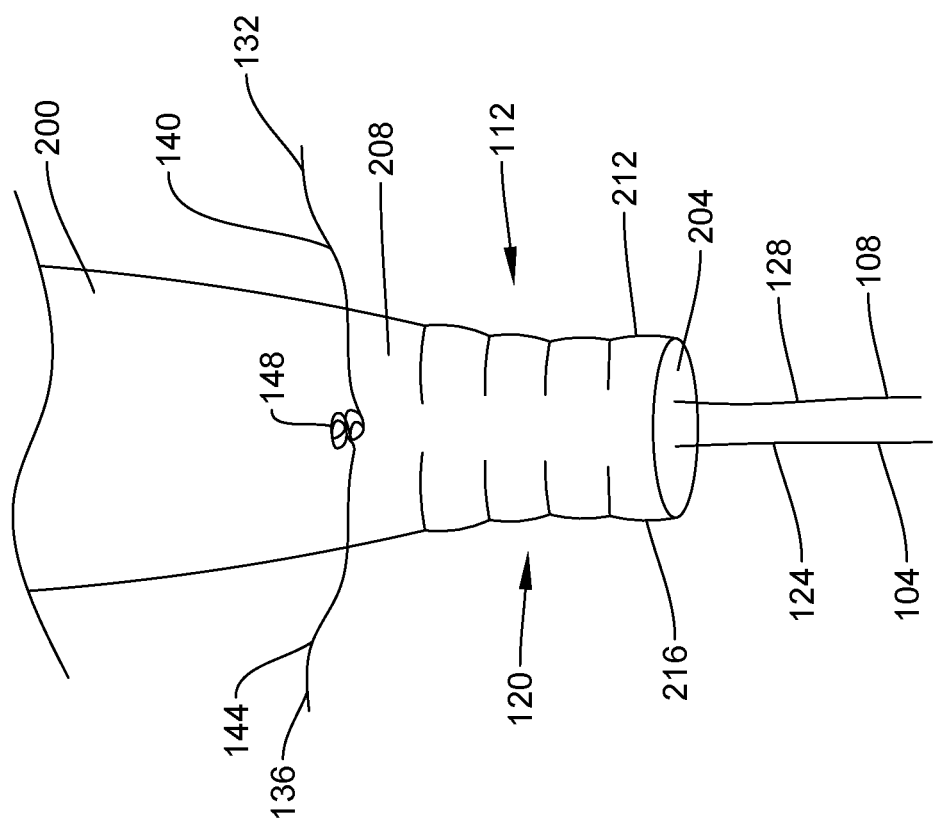
FIG. 2d is similar to FIG. 2c, but after the third and fourth free ends of the strand have been secured together.
Figure 2C:
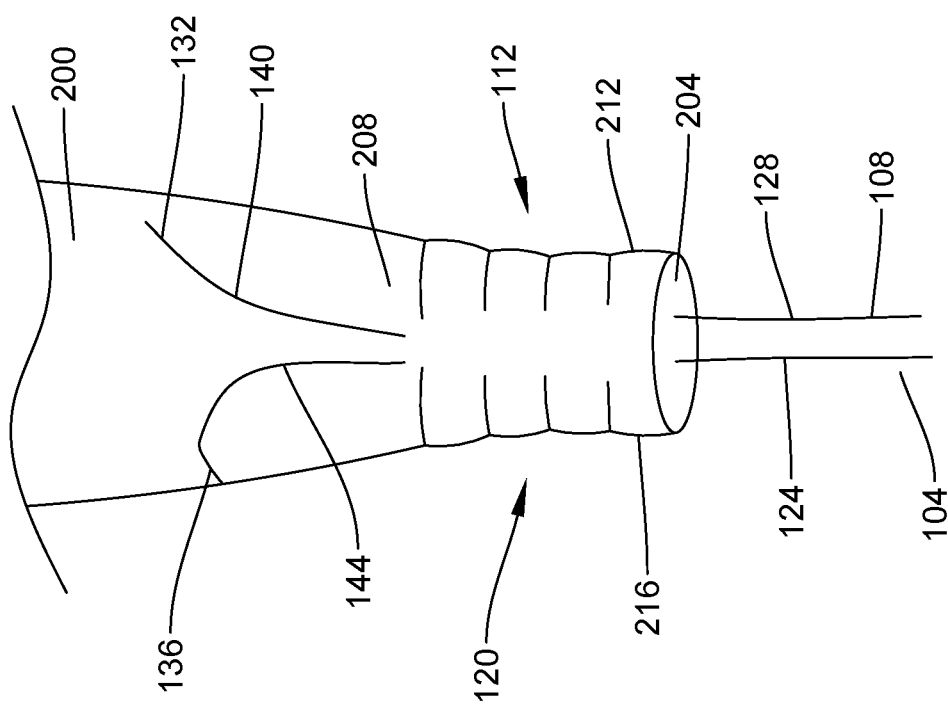
FIG. 2c is similar to FIG. 2b, but after the loop has been severed to create third and fourth free ends of the strand.
Figure 4:
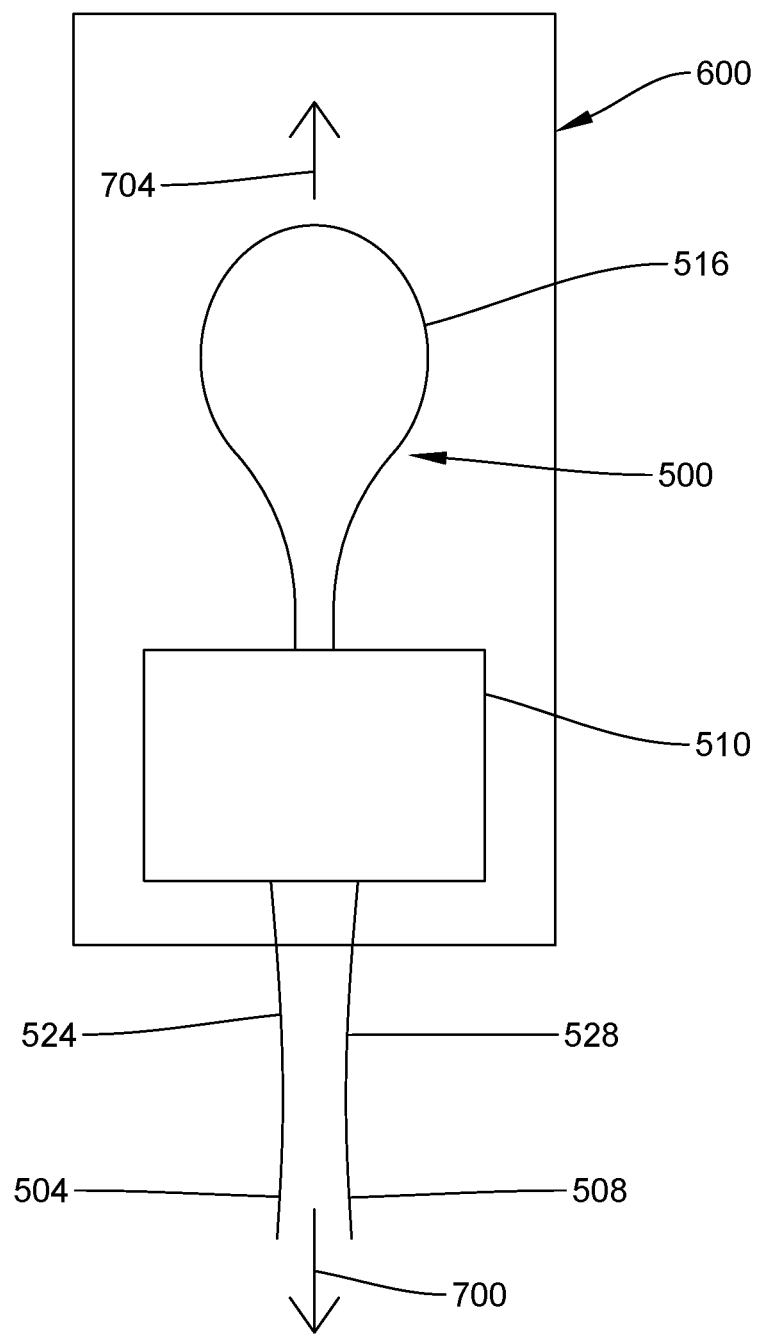
FIG. 4 is a schematic block illustration of a piece of tissue and a flexible strand somewhat similar to FIG. 1d.

FIG. 4 illustrates a flexible strand 500 anchored into tissue 600 and is presented to convey that the tissue 600 and specific stitching arrangement 510 are not necessarily limited to that illustrated in FIGS. 1a-3. For instance, while the flexible strand 500 includes a first free end 504 (e.g., first free end 104), first portion 524 (e.g., first portion 124), second free end 508 (e.g., second free end 108), second portion 528 (e.g., second portion 128), and a loop 516 (e.g., loop 116), the stitching arrangement 510 is represented by a generic box to indicate that it is not limited to the specific first and second series 112, 120 of stitches illustrated in FIGS. 1a-3. As one example, one or more stitches of any appropriate configuration may be disposed between the second portion 528 of the strand 500 and the loop 516 but not between the loop 516 and the first portion 524 of the strand 500. As another example, one or more stitches of any appropriate configuration may be disposed between the first portion 524 of the strand 500 and the loop 516 but not between the loop 516 and the second portion 528 of the strand 500. As a further example, different numbers and/or configurations of stitches may be disposed between the first portion 524 of the strand 500 and the loop 516 and between the loop 516 and the second portion 528 of the strand 500. Furthermore, the tissue 600 is represented by a generic box to indicate that it is not limited to the specific tissue 200 illustrated in FIGS. 1a-3.

Figure 6A:
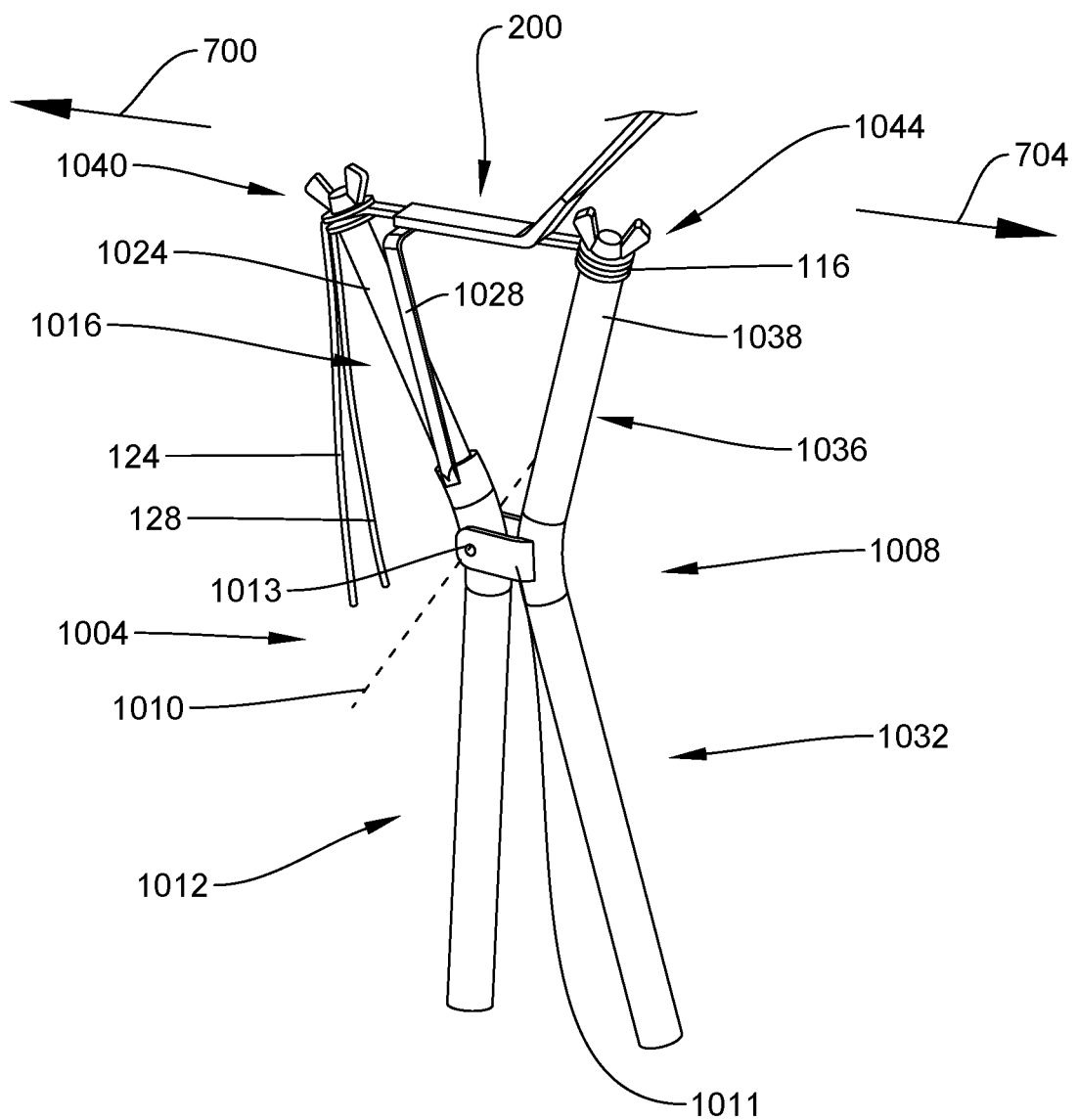
FIG. 6a is a first perspective view of a tool for use in applying first and second substantially opposite forces to the suture construct of FIG. 1d, according to one embodiment.
Figure 6B:
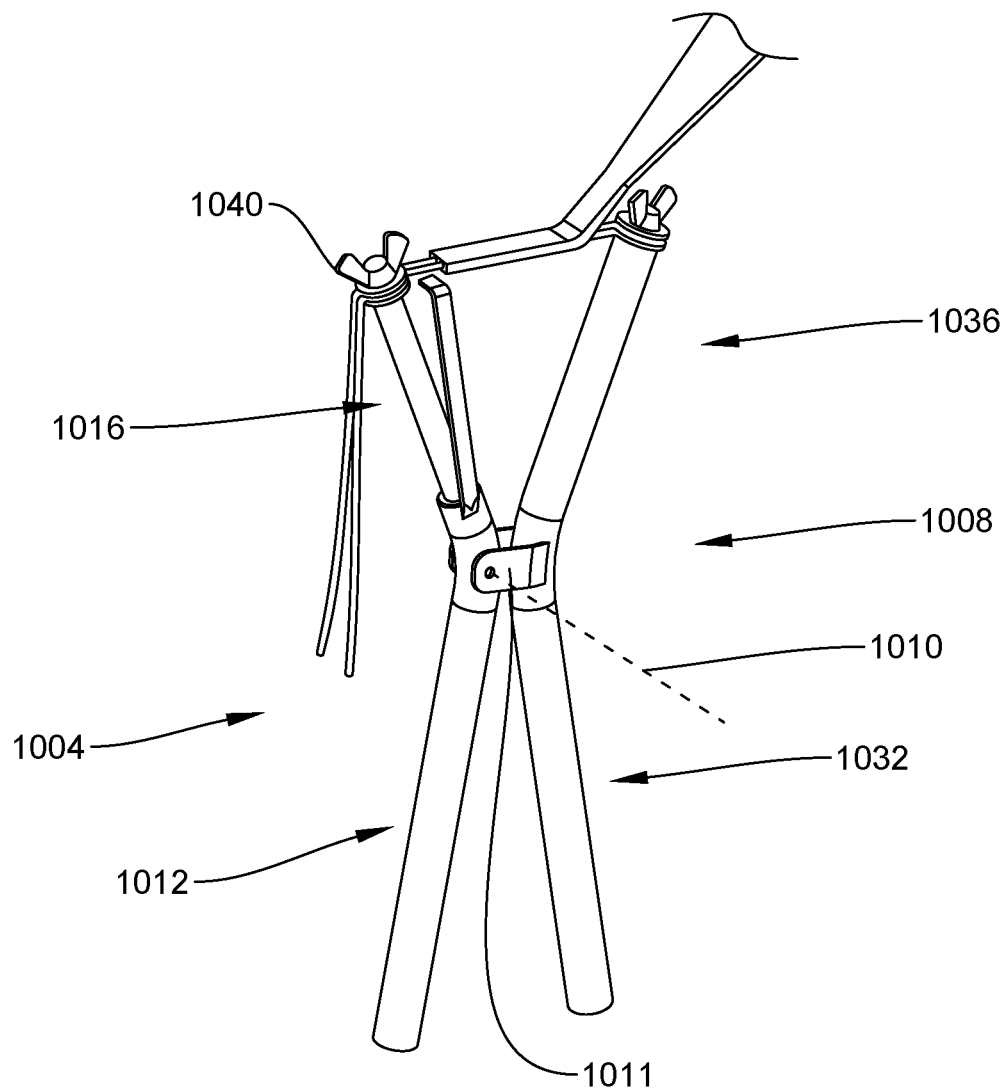

The first and second forces 700, 704 can be applied 636 to reduce slack in the suture construct as discussed above in any appropriate manner. In one arrangement, any appropriate tool or mechanical device may be used to simultaneously apply the first and second forces 700, 704. Turning now to FIGS. 6a-6b, perspective views of a tool 1000 for use in applying a tension to a suture construct are presented, according to one embodiment. Broadly, the tool 1000 includes a first portion 1004 that is pivotally attached to or relative to a second portion 1008 for pivotal movement about a pivot axis 1010 to apply a tension load to a suture construct to remove slack therein. As one example, one or more brackets 1011 (e.g., plates, bars, etc.) may pivotally secure the first portion 1004 to the second portion 1008. For instance, each bracket 1013 may be rigidly (non-movably) secured to the second portion 1008 and pivotally secured to the first portion 1004 via pivot pin 1011 or the like. As another example, each bracket 1011 may also be pivotally secured to the second portion 1008 of the tool 1000 such that each of the first and second portions 1004, 1008 are pivotal relative to each other and relative to the bracket(s) 1011. Other manners of pivotally securing the first portion 1004 relative to the second portion 1008 are also envisioned and encompassed herein.

As shown, the first portion 1004 may generally have a first handle member 1012 that is interconnected to a first arm 1016 such that manipulation of the first handle member 1012 about the pivot axis 1010 induces movement of the first arm 1016 about the pivot axis 1010. More specifically, the first arm 1016 may generally include an extension member 1024 (e.g., post, bar, bracket) that is configured to receive a first portion of a suture construct (e.g., such as the first and second portions 124, 128 of FIGS. 1a-3) and an indicator member 1028 that is configured to receive a contact from the extension member 1024 when a specific, predetermined level of tension has been applied to the suture construct as discussed in more detail below. The second arm 1036 may also include an extension member 1038 (e.g., post, bar, bracket) that is configured to receive a second portion of a suture construct (e.g., such as the loop 116 of FIGS. 1a-3).

The first and second extension members 1024, 1038 may include respective attachment mechanisms 1040, 1044 that are configured to secure (e.g., non-movably secure) the respective portions of the suture construct thereto. As just one example, each attachment mechanism 1040, 1044 may be in the form of a clamping arrangement such as a wing nut that is threadable along a threaded member (e.g., bolt), where a portion of the suture construct may be placed between the top of the respective extension member 1024, 1038 and the nut and then the nut may be tightened down against the portion of the suture construct to non-movably secure the portion relative to the respective extension member 1024, 1038. However, various other forms of the attachment mechanism 1040, 1044 are envisioned and encompassed herein.

Figure 7A:
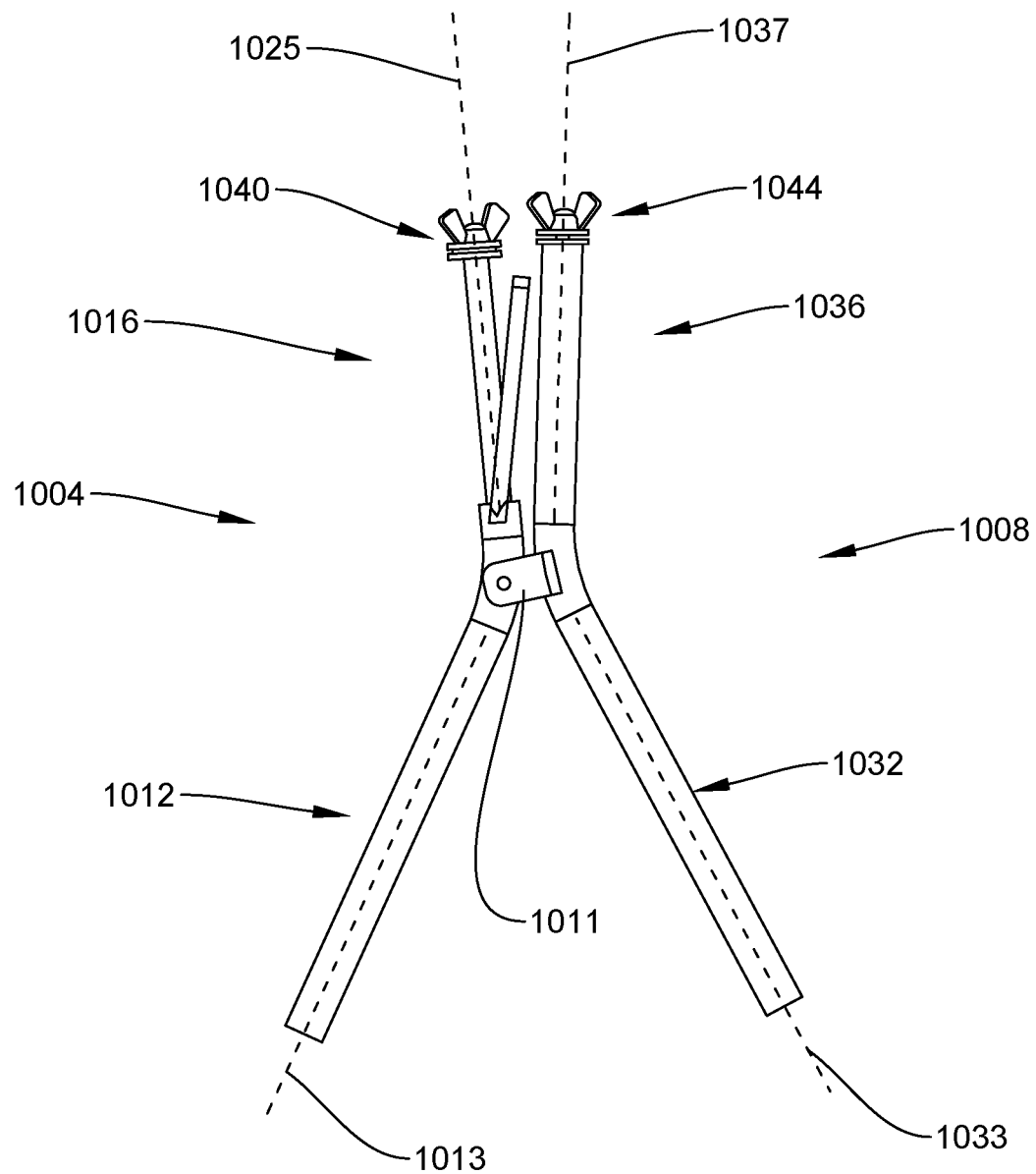
FIG. 7a is a first plan view of the tool of FIG. 6a with first and second portions of the tool being in a first position relative to each other.
Figure 7B:
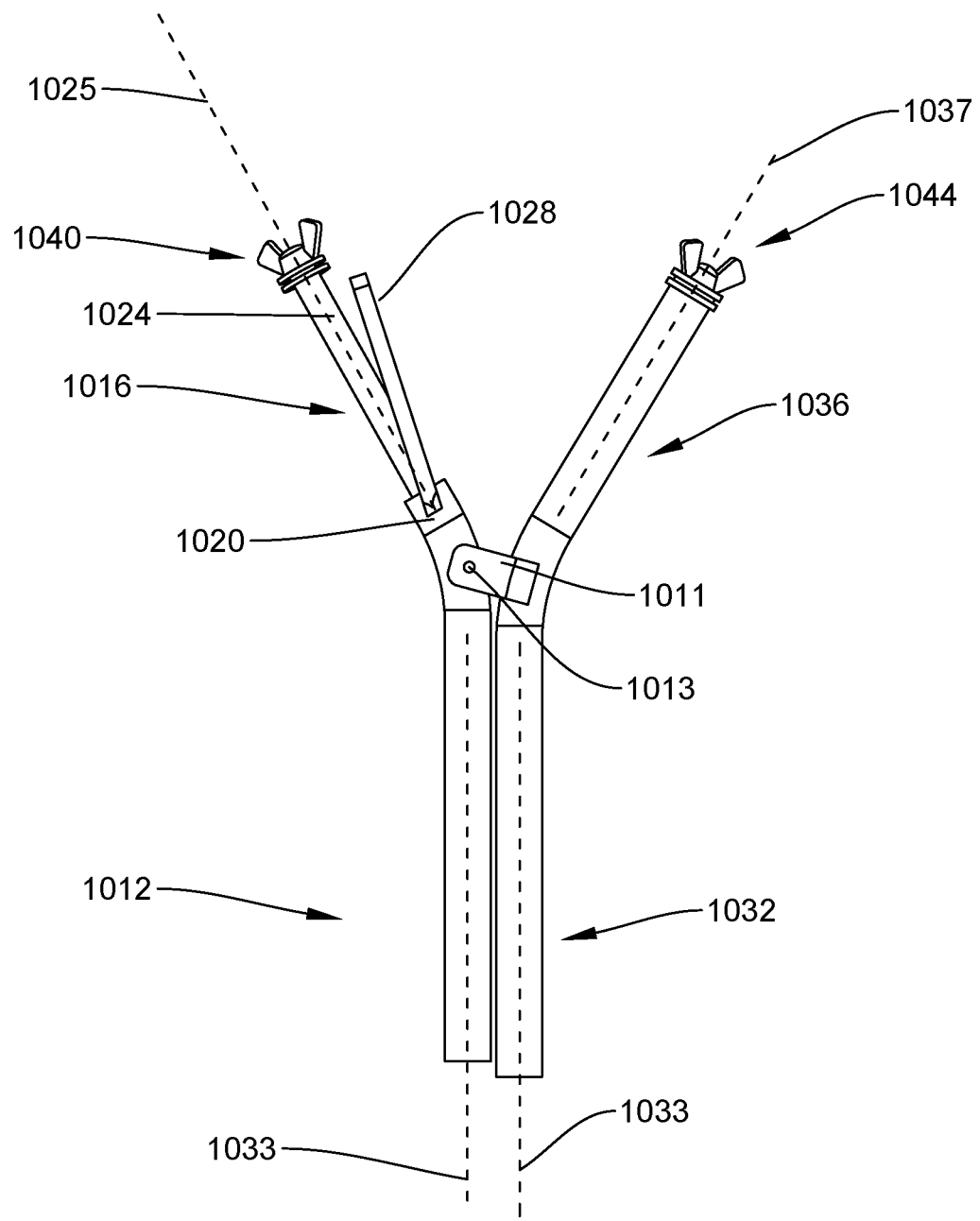
FIG. 7b is a second plan view of the tool of FIG. 6a with first and second portions of the tool being in a second position relative to each other.
Figure 8:
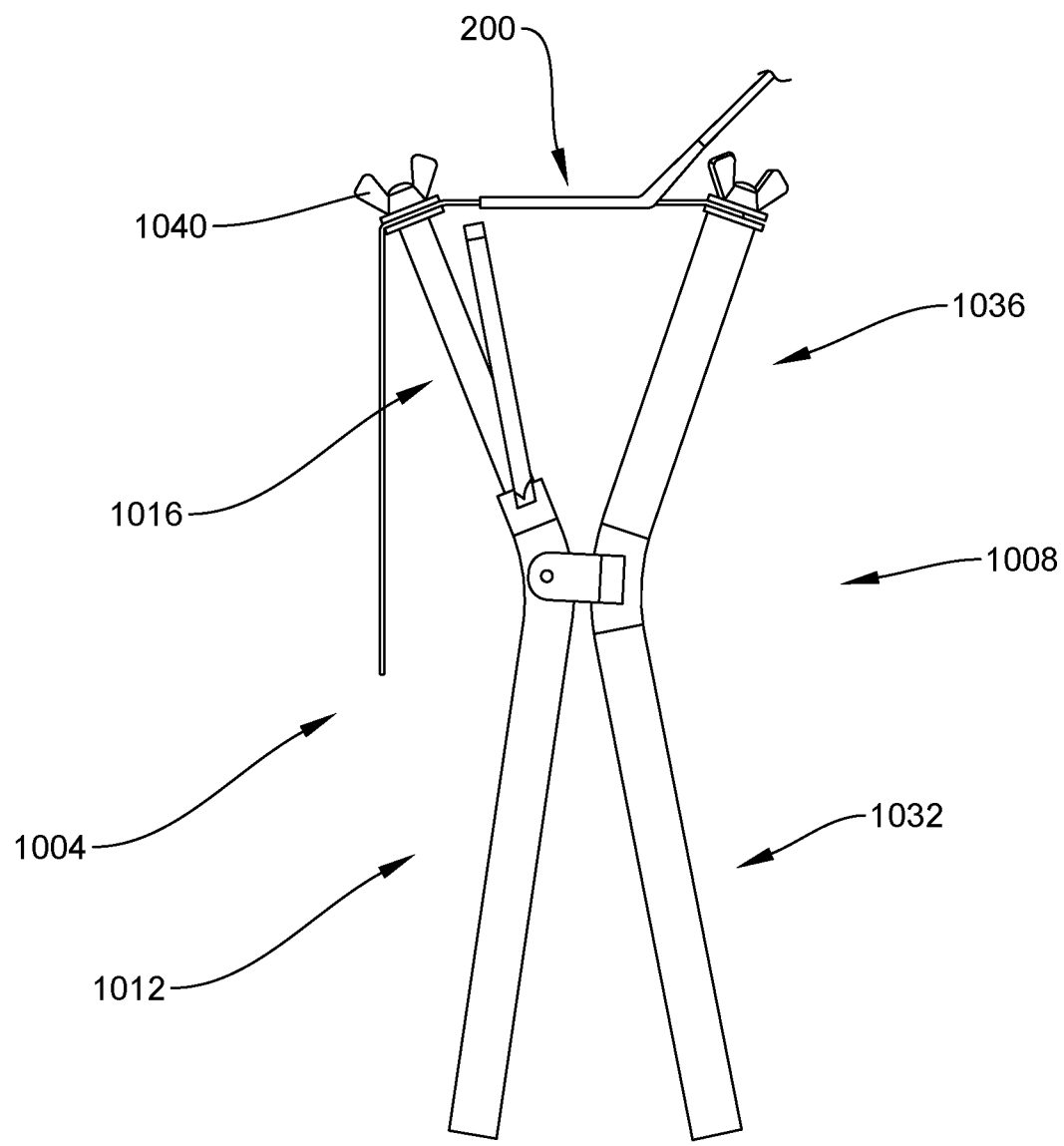
FIG. 8 is an elevation view similar to FIG. 6b.

FIGS. 7a-7b illustrate one range of motion of the tool 1000. For instance, FIG. 7a illustrates one position whereby the first handle member 1012 has been moved away from the second handle member 1032 until the first arm 1016 has contacted or is close to the second arm 1036 (e.g., via pivoting of the first portion 1004 in a first direction about the pivot axis 1010 relative to the second portion 1008). FIG. 7b illustrates another position whereby the first handle member 1012 has been moved towards the second handle member 1032 (e.g., via squeezing the first handle member 1012 against the second handle member 1032) so as to spread or move the first arm 1016 away from the second arm 1036 (e.g., via pivoting of the first portion 1004 in an opposite second direction about the pivot axis 1010 relative to the second portion 1008). The first handle member 1012 and first arm 1016 have respective longitudinal axes 1013, 1025 that are non-collinear and non-parallel (e.g., and that may form an obtuse angle therebetween) and the second handle member 1032 and second arm 1036 have respective longitudinal axes 1033, 1037 that are non-collinear and non-parallel (e.g., and that may form an obtuse angle therebetween) to facilitate the above range of motion.

In operation, and after a suture construct has been anchored into tissue such that a loop 116/516 is disposed on one end of the construct and first and second portions 124/524, 128/528 are disposed on an opposite end of the construct (e.g., as in FIGS. 2a, 3, and 4), the loop 116/516 may be secured to the second arm 1036 (e.g., via the second attachment mechanism 1044). Additionally, the tool 1000 may be manipulated to a position between the positions illustrated in FIGS. 7a-7b to allow the middle of the suture construct (e.g., the stitching arrangement 510, such as the first and second series 112, 120 of stitches) to be positioned between the first and second arms 1016, 1036 (or the first and second attachment members 1040, 1044) and the first and second portions 124/524, 128/528 to be secured on the first arm 1016 (e.g., via the first attachment mechanism 1040). See FIGS. 6a, 6b, 8, and 9.

Thereafter, a surgeon or other personnel may squeeze or otherwise move the first handle member 1012 towards the second handle member 1032 to induce the first arm to apply a first force (e.g., first force 700) to the first and second portions 124/524, 128/528 and an opposite second force (e.g., second force 704) to the loop 116/516 to apply a tension to the suture construct (i.e., to the stitching arrangement 510, such as the first and second series 112, 120 of stitches) to reduce slack in the construct in a manner that is substantially free of pulling or tugging on muscles and other surrounding body structures and that allows surgeons to apply greater levels of tension (e.g., 50 lbf or more) to the construct than they may otherwise be able to by hand. In one arrangement, use of the disclosed suture construct and tool 1000 may result in a reduction in post-repair gap formation from about 9 mm (e.g., with prior suture constructs) down to about 3 mm or less.

Before a suture construct is loaded or mounted onto the tool 1000, substantially the entirety of the first extension member 1024 and indicator member 1028 may move in unison as the first portion 1004 pivots about the pivot axis 1010 relative to the second portion 1008. Even after a suture construct has been loaded onto the tool 1000 as discussed above and a surgeon or other personnel has initially begun squeezing the first and second handle members 1012, 1032 so as to initially spread apart the first and second arms 1016, 1036 to apply an initial tension to the suture construct, the first extension member 1024 and indicator member 1028 may also move in unison. Furthermore, the extension member 1024 and indicator member 1028 may be spaced from each other such that a gap 1029 exists between a portion of the extension member 1024 and a contact portion 1030 of the indicator member 1028. In one arrangement, the gap 1029 may be at least 1 mm, such as at least 2 mm. In another arrangement, the gap 1029 may be no greater than 15 mm, such as no greater than 20 mm.

However, the first arm 1016 may be designed in any appropriate manner so as to begin to move or deflect (bend) relative to the indicator member 1028 (where the indicator member 1028 is not receiving a direct load from the suture construct as is the extension member 1024) upon the tension in the suture construct exceeding a first tension level and to contact the indicator member 1028 (e.g., at contact portion 1030 of contact area 1035) upon the tension in the suture construct reaching a second tension level that is higher than the first tension level (but less than the ultimate strength of the material(s) of the flexible strand 100, 500 making up the suture construct). For instance, a first end of the extension member 1024 adjacent the attachment mechanism 1040 and first and second portions 124, 128 of the strand 100 may experience a greater level of deflection than portions of the extension member 1024 farther down the extension member 1024 towards an opposite end of the extension member 1024 adjacent the handle member 1012 (e.g., which may experience little or no deflection).

The second or "optimal" tension level can be determined in any appropriate manner (e.g., based on biomechanical laboratory studies) to remove greater amounts of slack in the construct for inhibiting subsequent post-repair gap formation. In this regard, upon a surgeon squeezing the first and second handle members to apply a tension to the suture construct and the extension member 1024 moving and contacting the indicator member 1028, the surgeon may then release the first handle member 1012 whereupon the surgeon may know that the "optimal" tension has been applied to the suture construct upon such contact between the extension member 1024 and the indicator member 1028. After removal of the pre-tensioned suture construct and tissue from the tool 1000, the loop 116/516 may be severed and tied down as discussed above and then the first and second portions 124/524, 128/528 may be secured in any appropriate manner to an adjacent tissue, bone, and/or the like.

As discussed above, frictional forces between the flexible strand 100/500 and the tissue as well as severing the loop 116/516 and tying down the third and fourth portions 140, 144 of the strand 100 against the tissue 200 may substantially maintain the suture construct in this "pre-tensioned" state. In the case where it is known that the flexible strand 100/500 may slightly recoil or relax upon the surgeon releasing the first handle member 1024, one or more of the dimensions of the indicator member 1028, extension member 1024, spacing therebetween, other properties, etc. may be configured such that the second tension level is slightly higher than the "optimal" tension level such that upon any such recoiling or releasing, substantially the optimal tension level is present in the suture construct.

In one arrangement, the indicator member 1028 may be attached to a piece or component of the first portion 1004 that has a greater bending stiffness than that of the extension member 1024. As shown in FIGS. 6a-9b, for instance, the indicator member 1028 may be directly attached to a base member 1020 (e.g., collar, bracket, etc.) of the first arm 1016 that is constructed of one or more materials that collectively have a greater bending stiffness than that of the one or more materials making up the extension member 1024. As an example, the extension member 1024 may be constructed of aluminum while the base member 1020 may be constructed of stainless steel. Additionally or alternatively, one or more dimensions of the extension member 1024 and base member 1020 may be selected to impart the desired bending stiffness to the extension member 1024 (e.g., by designing the extension member 1024 to have a diameter or maximum cross-dimension that is less than that of the base member 1020). Furthermore, the extension member 1024 may be substantially directly attached to the base member 1020 as illustrated (in any appropriate manner, such as via fastener 1031 or the like), but independent from the connection between the indicator member 1028 and the base member 1020. Stated differently, the extension member 1024 and indicator member 1028 may be independently attached to the base member 1020.

Figure 9B:
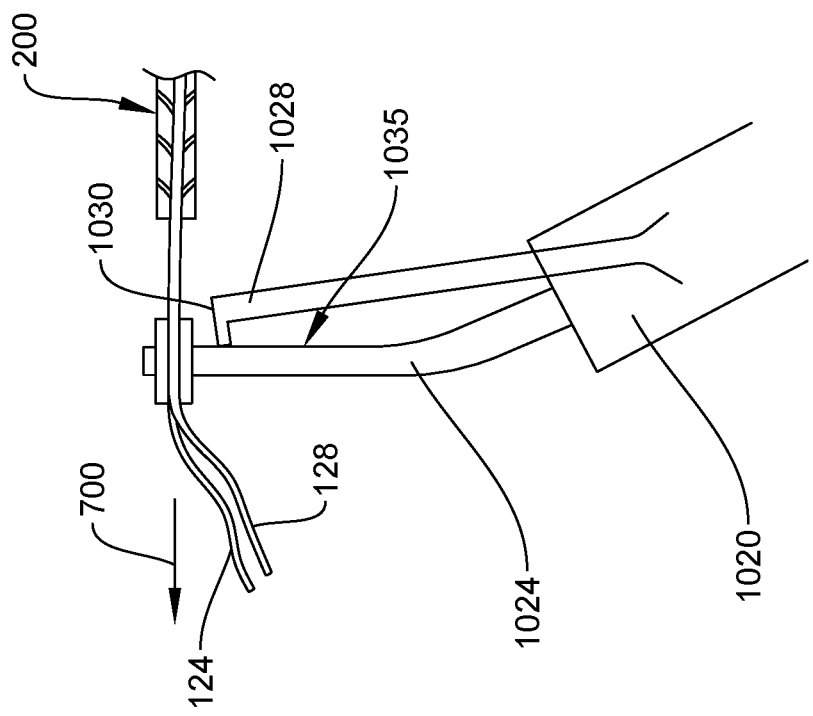
FIG. 9b is similar to FIG. 9a but after the tool has been manipulated to apply a tension to the suture construct and the extension member has deflected to contact the indicator member.
Figure 9A:
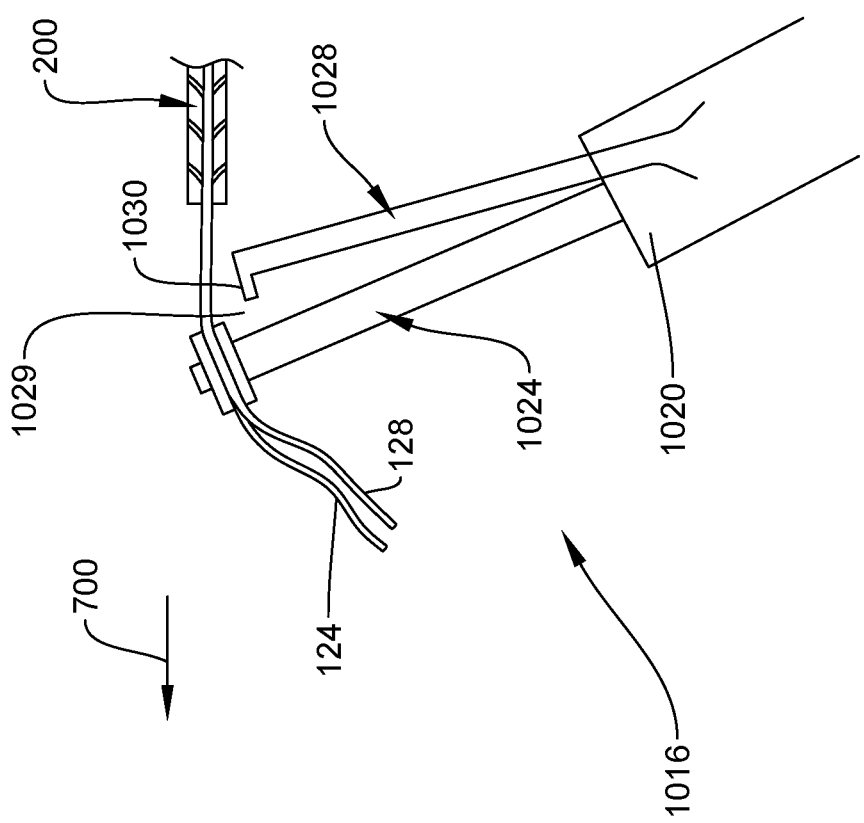
FIG. 9a is close-up view of a first arm of the first portion of the tool of FIG. 6a with a suture construct being attached to an extension member and the extension member being in a first position relative to an indicator member.
Figure 10A:
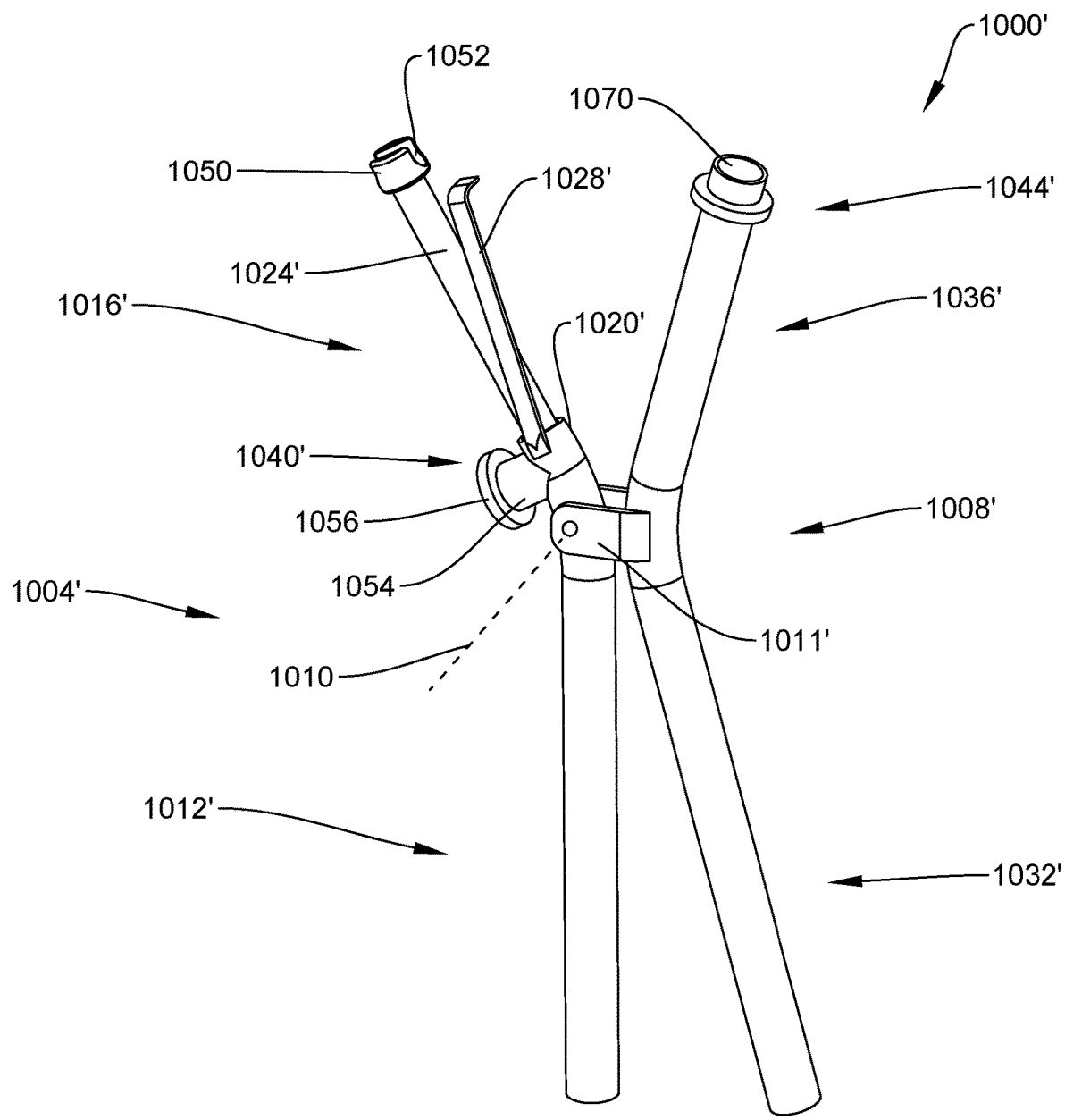
FIG. 10a is a first perspective view of a tool for use in applying first and second opposite forces to the suture construct of FIG. 1d, according to another embodiment.
Figure 10B:
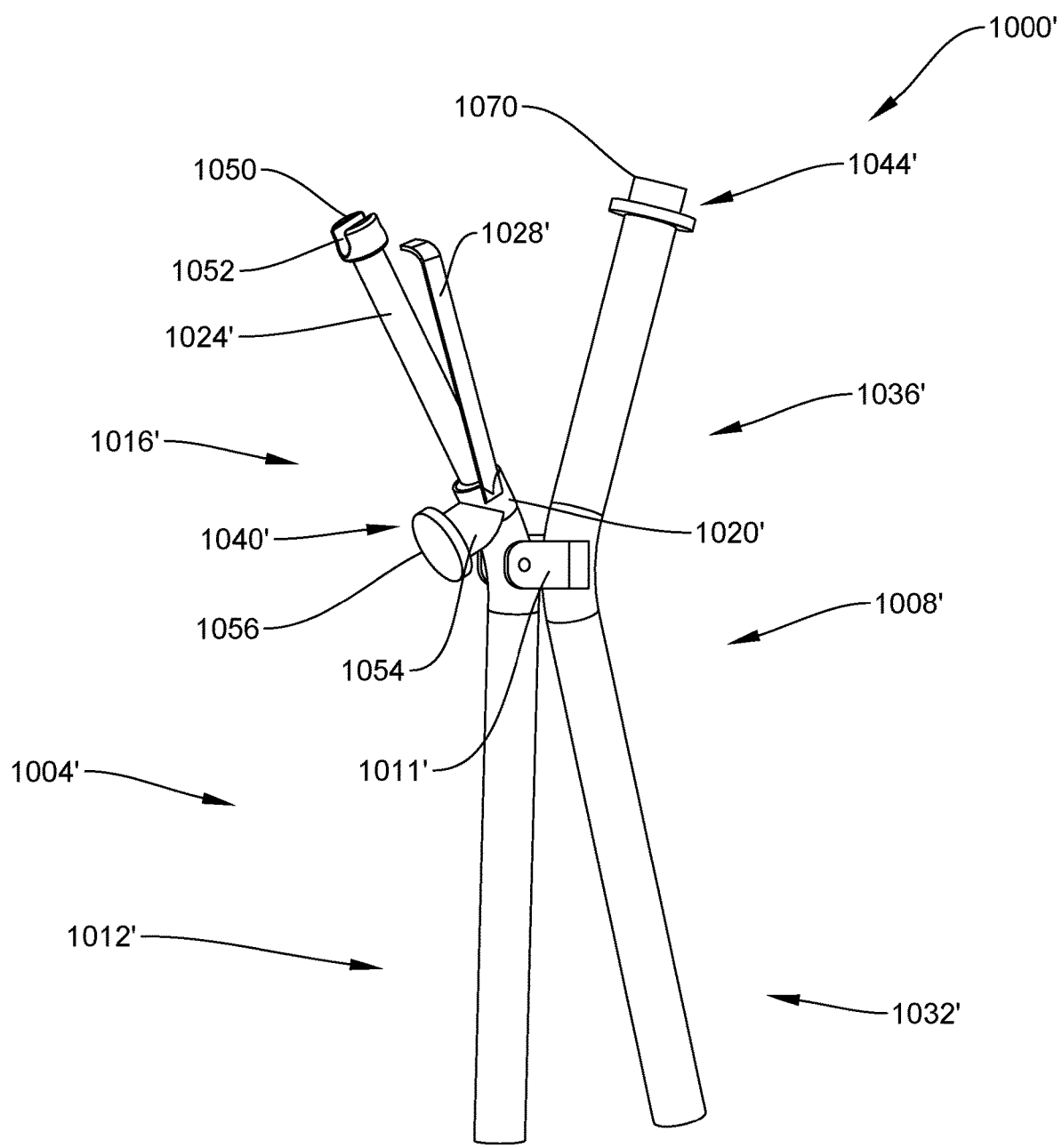
Figure 11A:
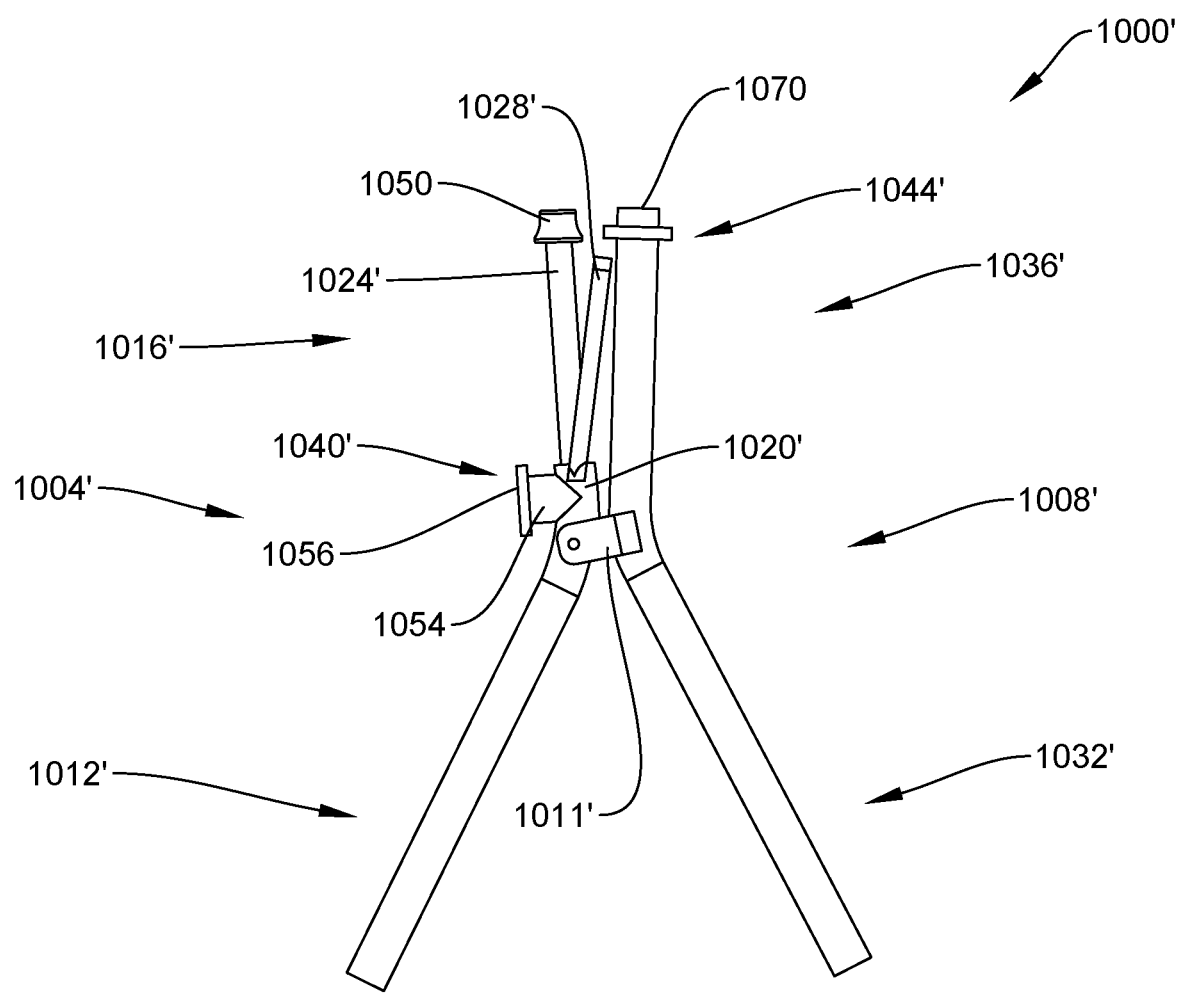
FIG. 11a is a first plan view of the tool of FIG. 10a with first and second portions of the tool being in a first position relative to each other.
Figure 11B:
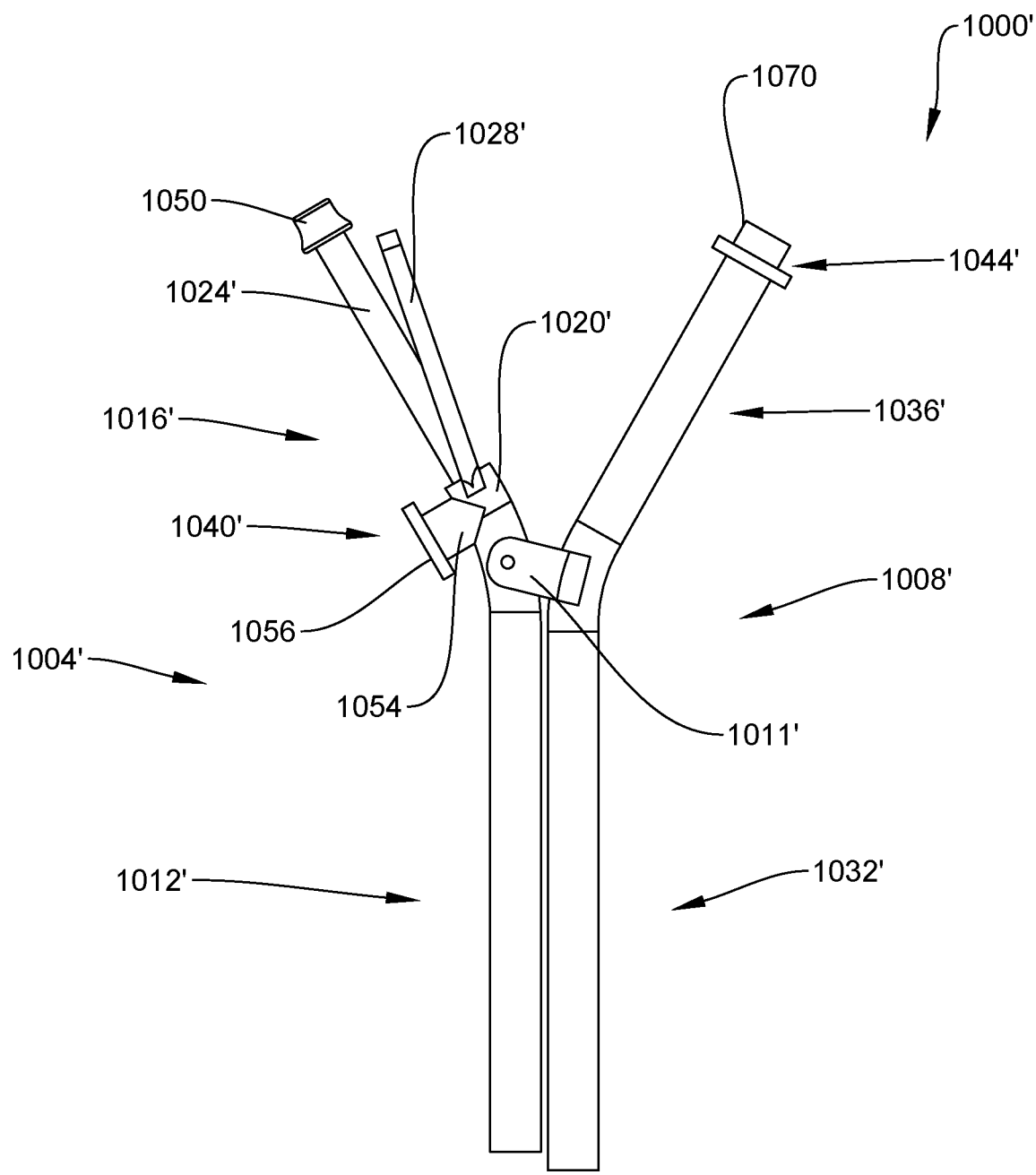
FIG. 11b is a second plan view of the tool of FIG. 10a with first and second portions of the tool being in a second position relative to each other.
Figure 12:
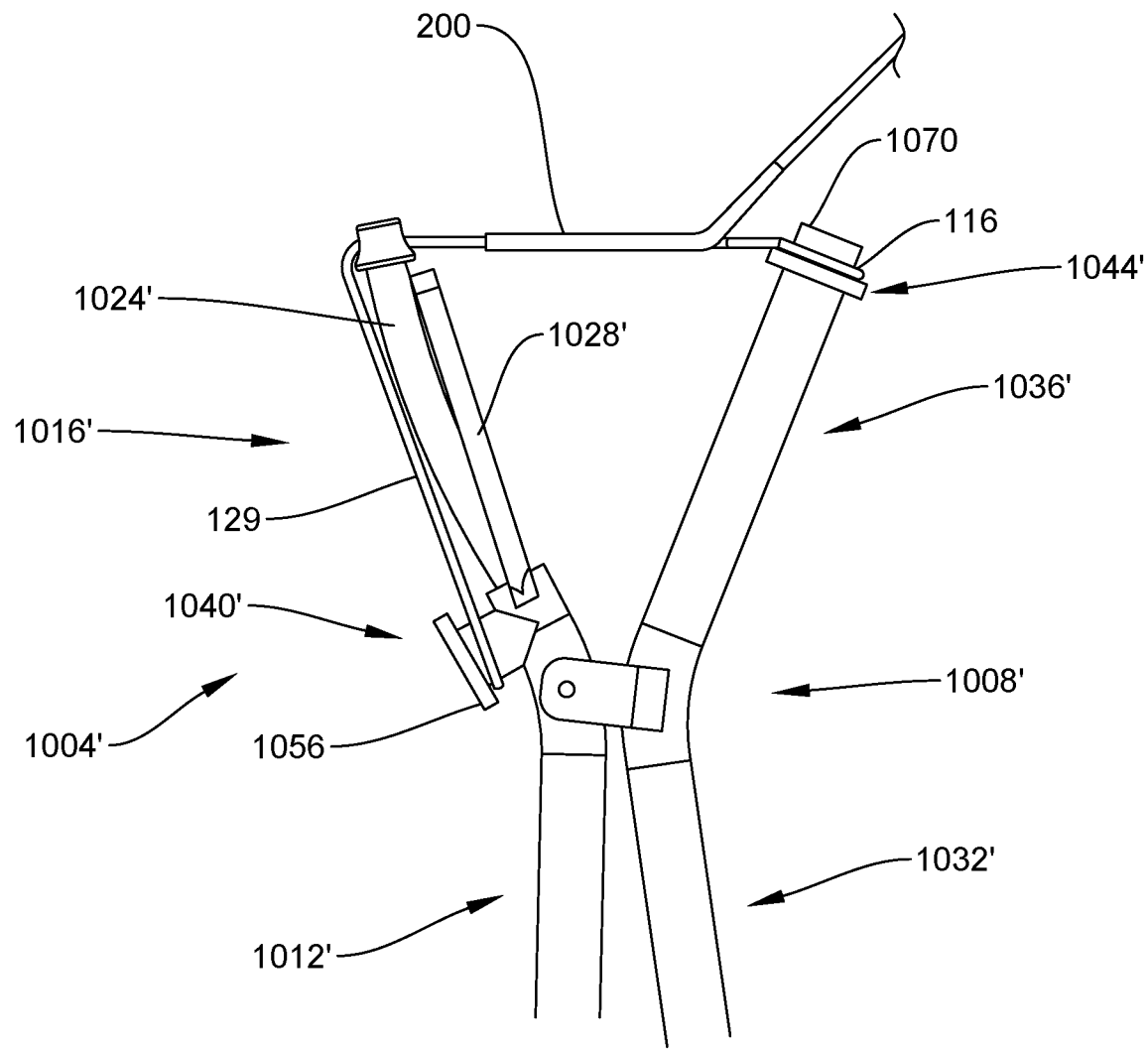
FIG. 12 is a close up view of the first and second arms of the tool of FIG. 10 and illustrating a suture construct and portion of tissue being attached to the first and second arms and the extension member being in contact with the indicator member.
Figure 13A:
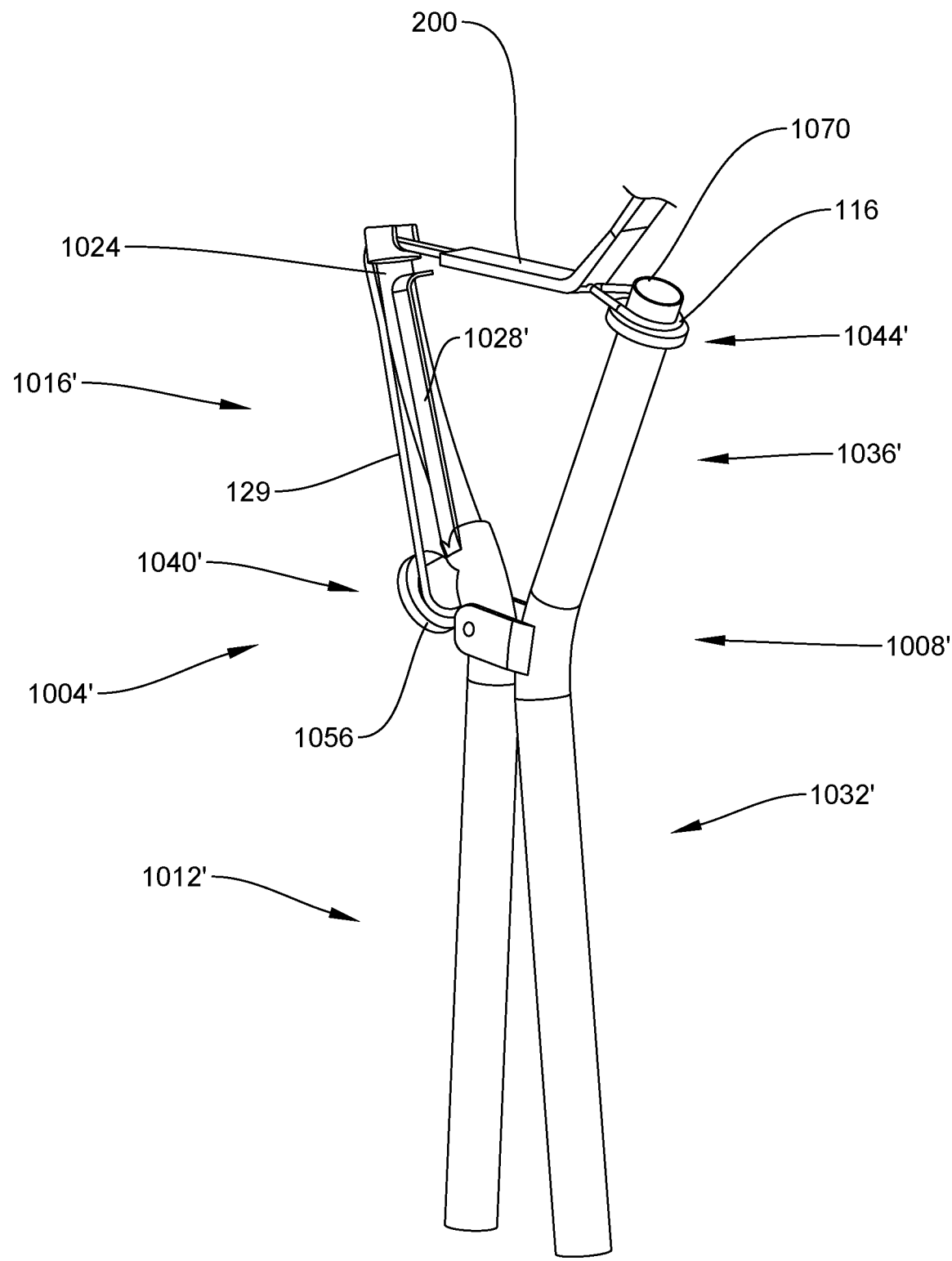
FIG. 13a is a first perspective view of the tool of FIG. 10a with a suture construct and portion of tissue being attached to the first and second arms and the extension member being in contact with the indicator member.
Figure 13B:
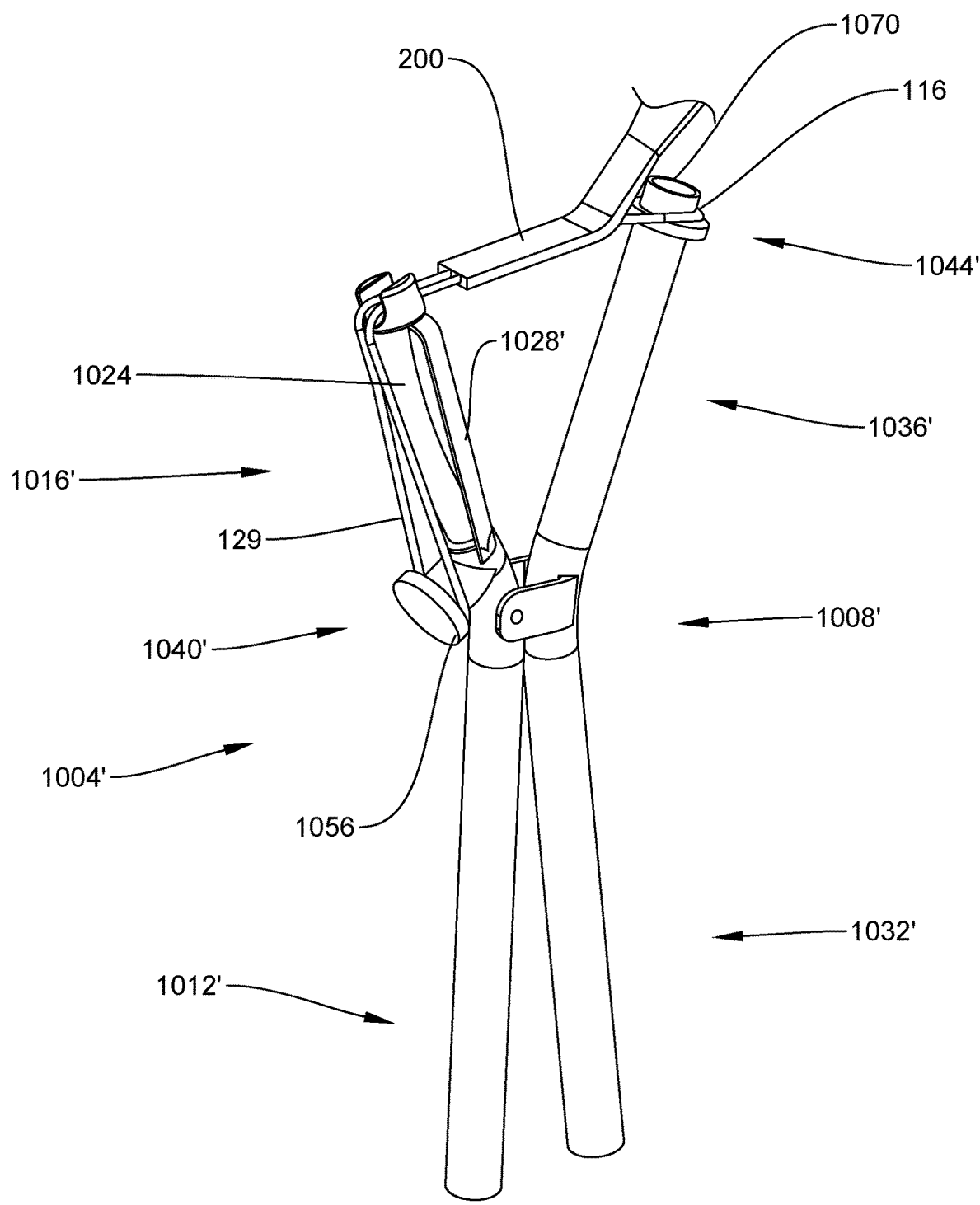

In this regard, upon the tension in the suture construct exceeding the above-noted first tension level, the above relative differences in bending stiffnesses may allow the extension member 1024 to bend and deflect towards the indicator member 1028 and eventually contact the indicator member 1028 upon the tension reaching the predetermined second tension level (e.g., see FIG. 9*b*, where the amount of bending of the extension member 1024 has been exaggerated for purposes of illustration). While the base member 1020 is illustrated in the figures as being a separate component that is attached to the first handle member 1012, this need not necessarily be the case. In one arrangement, the base member 1020 may be integral and/or one-piece with the first handle member 1012, whereupon the first handle member 1012 may have a bending stiffness greater than that of the extension member 1024 (e.g., by selecting particular materials, dimensions, etc.).

While differences in relative bending stiffnesses between components of the first portion 1004 have been discussed as one manner to allow movement of the extension member 1024 relative to the indicator member 1028, various other arrangements for allowing such movement are envisioned as well such as a pivotal connection between the extension member 1024 and the base member 1020 (or first handle member 1012) that is normally biased away from the indicator member 1028 by one or more springs (having one or more particular spring constants) to maintain the gap 1029 in the absence of a tension being applied to the suture construct. In this case, the extension member 1024 may overcome the spring force and move to contact the indicator member 1028 upon the tension in the suture construct exceeding the first tension level and eventually reaching the second tension level.

It is to be understood that one or more various parameters of the tool 1000 may be selected, modified, or configured as appropriate so that the extension member 1024 is configured to deflect and contact the indicator member 1028 substantially upon the second tension level in the suture construct being reached. For instance, these parameters may include but are not necessarily limited to the specific material(s) making up the various components (e.g., so as to achieve particular bending stiffnesses), dimensions of various components, spacing or relative positioning between components (e.g., angle between the indicator member 1028 and the extension member 1024), and the like.

FIGS. 10*a*-13*b* illustrate a tool 1000' according to another embodiment, where like reference numerals indicate similar components. One difference between the tool 1000 of FIGS. 6*a*-9*b* and the tool 1000' is that the attachment mechanism 1044' includes a protrusion 1070 about which the loop 116 of the strand 100 can be disposed (e.g., rather than a clamping mechanism). Another difference is that the attachment mechanism 1040' includes a protrusion 1054 about which the first and/or second portion 124, 128 of the strand 100 can be disposed (e.g., rather than a clamping mechanism). For instance, the first and second portions 124, 128 can be secured together (e.g., via one or more knots, not shown) to form a loop 129 and the loop 129 can be disposed over the protrusion 1054. As shown, the protrusion 1054 may be secured to the base member 1020' and/or a portion of the first handle member 1012 or in other words not to the extension member 1024' so that the protrusion 1054 does not deflect towards the indicator member 1028' upon deflection of the extension member 1024'. In one arrangement, a stop member 1056 (e.g., rim) may be attached to an end of the protrusion 1054 to inhibit inadvertent removal of the loop 129 from the protrusion. While not shown, a similar stop member may also be attached to the protrusion 1070.

As shown, the first and second portions 124, 128 of the strand 100 can be passed or slid through a channel 1052 of a guiding member 1050 that is attached to the extension member 1024' (at a first or upper end of the extension member 1024') before transitioning into the loop 129. Furthermore, the attachment mechanism 1040' may be spaced from the guiding member 1050 as illustrated so that after passing through or over the guiding member 1050, the strand 100 may extend along the extension member 1024 before wrapping around the protrusion 1054. Upon use of the tool 1000' to apply the desired tension to the suture construct, the suture construct may be removed from the tool 1000', the loop 129 may be severed to again create the first and second portions 124, 128 of the strand 100, and then the first and second portions 124, 128 may be attached to adjacent tissue and/or bone in any appropriate manner as discussed previously.

It will be readily appreciated that many deviations may be made from the specific embodiments disclosed in the specification without departing from the spirit and scope of the invention. For instance, while the present disclosure has been discussed in the context of the first and second portions 124/524, 128/528 of the strand 100 being disposed over the first arm 1016/1016' and the loop 116/516 of the strand 100 being disposed over the second arm 1036/1036', the suture construct could be reversed on the tool 1000/1000' such that the first and second portions 124/524, 128/528 are disposed over the second arm 1036/1036' and the loop 116/516 is disposed over the first arm 1016/1016'. As another example, more than one loop 116/516 may be included in the suture construct. For instance, after creating a first loop 116/516 as discussed, the first end 104/504 of the strand may be passed into an out of the second portion 208 of tissue 200/600 and one or more additional loops 116/516 could be created before creating the second series 120 of stitches.

As a further example, stiches could be created between the first portion 124/524 of the strand 100/500 and the loop 116/516 (e.g., on the second lateral side 216 of the tissue 200) and not between the second portion 128/528 of the strand 100/500 and the loop 116/516 (e.g., on the first lateral side 212 of the tissue 200) or vice versa. Furthermore, different numbers or configurations of stitches may be created adjacent the first and second lateral portions 212, 216 of the tissue 200. Still further, while the Krackow stitching method is discussed herein, the teachings herein may be applicable to numerous other stitching and suturing methods and constructs.

Certain features that are described in this specification in the context of separate embodiments can also be implemented in combination in a single embodiment. Conversely, various features that are described in the context of a single embodiment can also be implemented in multiple embodiments separately or in any suitable subcombination. Furthermore, methods discussed herein may be practiced with more, fewer, different steps than as specifically presented herein. Moreover, although features may be described above as acting in certain combinations and even initially claimed as such, one or more features from a claimed combination can in some cases be separated from the combination, and the claimed combination may be directed to a subcombination or variation of a sub combination.

I claim:

1. A system comprising:
a suture construct for use in the repair of a tissue, the suture construct including:
a first portion of a flexible strand configured to be disposed between a first portion of the tissue and a first free end of the flexible strand;
a second portion of the flexible strand configured to be disposed between the first portion of the tissue and a second free end of the flexible strand;
a series of stitches of the flexible strand that are configured to be cinched over a surface of the tissue;
a loop of the flexible strand protruding out of the second portion of the tissue, wherein the series of stitches is disposed between a) the loop and b) the first and second portions of the flexible strand;
a tool engaged with the suture construct including:
a first arm on which the first and second portions of the flexible strand are secured;
a second arm on which the loop of the flexible strand is secured, wherein the first arm is configured to be manipulated away from the second arm to simultaneously apply a) a first force to the first and second portions of the flexible strand and b) an opposite second force to the loop of the flexible strand for tightening the one or more stitches against the tissue and thereby reducing slack in the flexible strand;
a first handle member that is configured to be manipulated to force at least the first arm away from the second arm; and
an indicator member attached to the first handle member that is configured to be contacted by the first arm member when a desired tension has been applied to the suture construct between the loop and the first and second portions of the suture construct.

2. The system of claim 1, wherein the series of stitches are non-overlapping.

3. The system of claim 1, wherein the tool includes a second handle member such that squeezing the first handle member towards the second handle member forces at least the first arm away from the second arm.

4. The system of claim 3, wherein each of the first arm, second arm, first handle member, and second handle member includes a longitudinal axes, wherein the longitudinal axes of the first arm and first handle member are non-collinear and non-parallel, and wherein the longitudinal axis of the second arm and second handle member are non-collinear and non-parallel.

5. The system of claim 3, wherein the first arm and first handle member collectively comprise a first portion of the tool, wherein the second arm and second handle member collectively comprise a second portion of the tool, wherein the first and second portions of the tool are pivotally attached to each other at a pivot axis, and wherein squeezing the first handle member towards the second handle member pivots the first portion of the tool about the pivot axis.

6. A method of anchoring a suture construct into tissue, comprising:
inserting a first free end of a flexible strand into a first portion of a tissue;
using the first free end of the flexible strand to create one or more stitches in the tissue;
exiting a second portion of the tissue with the first free end of the flexible strand, the one or more stiches being disposed between the first and second portions of the tissue;
creating a loop with a portion of the flexible strand that has exited the second portion of the tissue;
inserting the first free end of the flexible strand into the second portion of the tissue;
maintaining at least a portion of the loop outside of the second portion of the tissue after inserting the first free end of the flexible strand into the second portion of the tissue;
exiting the first portion of the tissue with the first free end of the flexible strand; and
simultaneously applying a) a first force to i) a first portion of the flexible strand disposed between the tissue and the first free end of the flexible strand and ii) a second portion of the flexible strand disposed between the tissue and a second free end of the flexible strand and b) an opposite second force to the loop to tighten the one or more stitches against the tissue and thereby reduce slack in the flexible strand.

7. The method of claim 6, wherein the one or more stitches is a first series of stitches, and wherein the method further includes after the maintaining and before the exiting the first portion of the tissue with first free end of the flexible strand:
using the first free end of the flexible strand to create a second series of stitches in the tissue.

8. The method of claim 7, wherein the first series of stitches is disposed on a first lateral side of the tissue and the second series of stitches is disposed on an opposite second lateral side of the tissue.

9. The method of claim 8, wherein a reference plane passes through the tissue and intersects the first and second portions of the tissue, wherein the first lateral side is on one side of the reference plane and the second lateral side is on an opposite side of the reference plane, and wherein the first and second applied forces are parallel to the reference plane.

10. The method of claim 6, wherein a reference plane passes through the tissue and intersects the first and second portions of the tissue, wherein simultaneously applying the first force and the second opposite force are parallel to the reference plane and wherein applying the first force and second opposite force in a direction induces each of the one or more stitches to apply a cinching force about a slice of the tissue that is non-parallel to the reference plane to tighten the stitch against the tissue.

11. The method of claim 10, wherein each slice is substantially perpendicular to the reference plane.

12. The method of claim 6, further including:
mounting the first and second portions of the flexible strand on a first arm of a tool; and
mounting the loop of the flexible strand on a second arm of the tool, wherein the simultaneously applying includes: manipulating the tool to force at least the first arm away from the second arm to thereby apply the first and second forces.

13. The method of claim 6, further including after the simultaneously applying:
   severing the loop to create a) a third portion of the flexible strand between the tissue and a third free end of the flexible strand and b) a fourth portion of the flexible strand between the tissue and a fourth free end of the flexible strand; and securing the third and fourth portions of the flexible strand together against the tissue.

14. The method of claim 13, further including after the securing:
   securing the first and second portions of the flexible strand to another structure.

\* \* \* \* \*